United States Patent [19]
Weisman et al.

[11] Patent Number: 4,865,596
[45] Date of Patent: * Sep. 12, 1989

[54] COMPOSITE ABSORBENT STRUCTURES AND ABSORBENT ARTICLES CONTAINING SUCH STRUCTURES

[75] Inventors: Paul T. Weisman, Fairfield; Thomas H. Daugherty, Cincinnati, both of Ohio

[73] Assignee: The Procter & Gamble Company, Cincinnati, Ohio

[*] Notice: The portion of the term of this patent subsequent to Sep. 27, 2005 has been disclaimed.

[21] Appl. No.: 91,805

[22] Filed: Sep. 1, 1987

[51] Int. Cl.⁴ ............................................. A61F 13/16
[52] U.S. Cl. ...................................... 604/368; 604/370
[58] Field of Search ............... 604/368, 369, 370, 365, 604/366, 358, 372; 428/171, 172, 221, 224, 283

[56] References Cited

U.S. PATENT DOCUMENTS

| | | | |
|---|---|---|---|
| 3,016,599 | 1/1962 | Perry | 428/338 |
| 3,971,373 | 7/1976 | Braun | 128/146.2 |
| 4,100,324 | 7/1978 | Anderson et al. | 428/288 |
| 4,103,058 | 7/1978 | Humlicek | 428/171 |
| 4,118,531 | 10/1978 | Hauser | 428/224 |
| 4,145,464 | 3/1979 | McConnell et al. | 428/171 |
| 4,239,043 | 12/1980 | Gellert | 128/285 |
| 4,307,143 | 12/1981 | Meitner | 252/91 |
| 4,373,519 | 2/1983 | Errede et al. | 128/156 |
| 4,381,782 | 5/1983 | Mazurak et al. | 604/368 |
| 4,429,001 | 1/1984 | Kolpin et al. | 428/283 |
| 4,460,642 | 7/1984 | Errede et al. | 428/283 |
| 4,468,428 | 8/1984 | Early et al. | 428/221 |
| 4,604,313 | 8/1986 | McFarland et al. | 428/172 |
| 4,650,479 | 3/1987 | Insley | 604/358 |
| 4,755,178 | 7/1988 | Insley et al. | 604/366 |
| 4,773,903 | 9/1988 | Weisman et al. | 604/368 |

FOREIGN PATENT DOCUMENTS 156649 10/1985 European Pat. Off. .
2113731A 8/1983 United Kingdom .

Primary Examiner—C. Fred Rosenbaum
Assistant Examiner—Mark O. Polatta
Attorney, Agent, or Firm—George W. Allen; Jerry J. Yetter; Richard C. Witte

[57] ABSTRACT

The present invention relates to composite absorbent structures suitable for incorporation into absorbent articles such as sanitary napkins, diapers, incontinent devices, training pants and the like. Such structures comprise webs of entangled blown microfibers, substantially nonabsorbent crimped staple fibers, a fluid control system comprising hydrophilic particulate entities and also optionally containing certain types of hydrogel-forming polymeric gelling agent particles, and a hydrophilizing agent. Such composite web structures of this construction have especially desirable comfort, integrity and fluid handling characteristics.

20 Claims, 2 Drawing Sheets

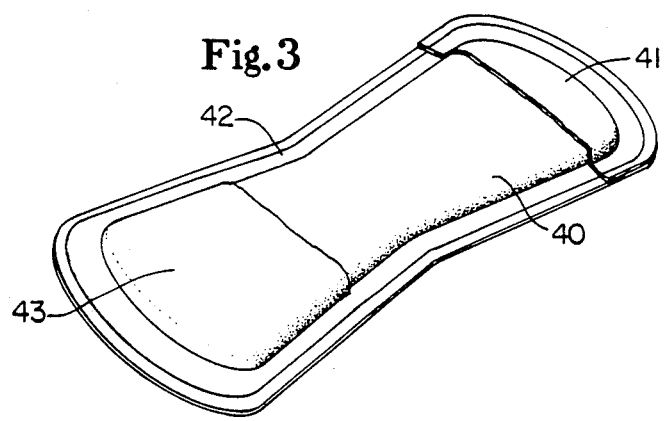
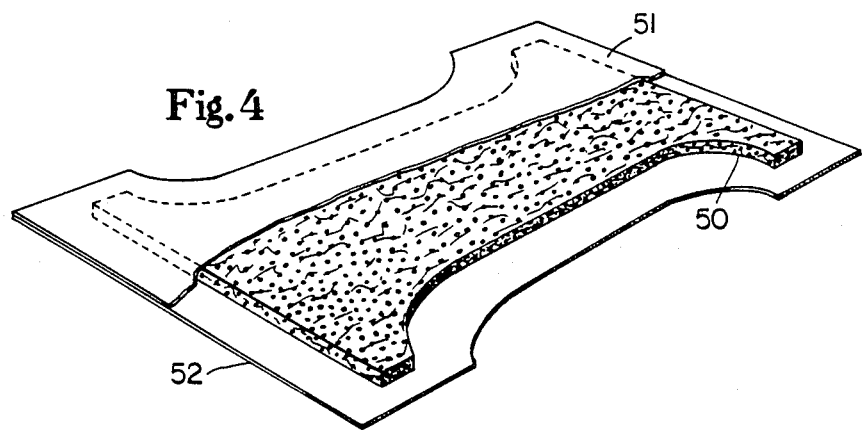
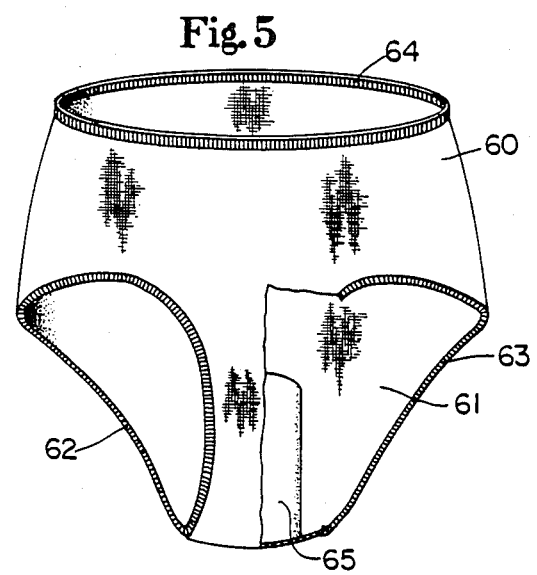

COMPOSITE ABSORBENT STRUCTURES AND ABSORBENT ARTICLES CONTAINING SUCH STRUCTURES

BACKGROUND OF THE INVENTION

The present invention relates to composite structures suitable for absorbing discharged body fluids. Such structures can be incorporated into disposable absorbent articles such as sanitary napkins, infant diapers, adult incontinence pads and the like.

Absorbent structures which comprise entangled masses of fibers, i.e., fibrous webs, are well known in the art. Such structures can imbibe liquids, such as discharged body fluids, both by an absorption mechanism wherein fluid is taken up by the fiber material itself and by a wicking mechanism wherein fluid is acquired by, distributed through and stored in the capillary interstices between fibers.

While absorbent capacity is a significant factor in determining the suitability of absorbent structures for use in disposable absorbent articles, other factors can also be important. For disposable absorbent articles which are worn or positioned in a particular relationship to the user's body, mechanical properties of the absorbent structures utilized in such articles are likewise relevant considerations. Thus features such as flexibility; resilience, e.g., resistance to bunching; softness; and tear resistance must generally be taken into account when selecting appropriate types of absorbent structures for use in absorbent articles. Absorbent structure properties which determine the comfort of the absorbent articles incorporating such structures are especially important in products like sanitary napkins and adult incontinence pads wherein the intimate contact of the article with the wearer's body make the comfort properties of such structures especially noticeable.

One way of imparting strength and flexibility to fibrous web absorbent structures has involved the use of blown microfibers in combination with staple absorbent fibers to fashion absorbent products. Anderson et al, U.S. Pat. No. 4,100,324; Issued July 11, 1978, for example, discloses preparation of absorbent "fabrics" fashioned from blown microfibers and wood pulp fibers. Technology has also been developed to enhance the absorbent capacity of microfiber/staple fiber webs by incorporating therein particles of fluid-absorbent polymeric material. For example, Kimberly-Clark Ltd., British Patent Spec. No. 2,113,731A, Published Aug. 10, 1983; Kolpin/Brownlee, U.S. Pat. No. 4,429,001, Issued Jan. 31, 1984 and Minnesota Mining & Manufacturing Company, European Patent Application EP-A-No. 156649, Published Oct. 2, 1985 all disclose sorbent sheet materials which comprise webs of entangled blown microfibers, generally absorbent staple fibers and particles of solid, high-sorbency, liquid-sorbent polymer materials.

While a number of prior art composite webs comprising microfibers, generally absorbent staple fibers and liquid-sorbent particles are quite useful as absorbent structures, the very materials used therein to provide absorbency tend to render such webs less resilient. However, one type of microfiber-based composite web structure which provides especially desirable resilience as well as useful absorbent capacity is disclosed in the copending U.S. patent application of Weisman, Daugherty and Insley, Jr., which application has Ser. No. 057,599 filed June 2, 1987, U.S. Pat. No. 4,773,903, issued Sept. 27, 1988. Composite web structures of this type utilize substantially nonabsorbent, crimped synthetic polymeric staple fibers to impart web flexibility and resilience and a particular type of polymeric gelling agent to impart absorbent capacity for aqueous body fluids.

Notwithstanding the existence of the foregoing kinds of microfiber-based composite absorbent structures, there is a continuing need to identify additional types of high capacity absorbent structures which contain microfiber and synthetic staple fibers to provide strength, integrity and resilience, and which also contain fluid control materials to manage the acquisition, distribution and retention of fluids by and within such absorbent structures. Accordingly, it is an object of the present invention to provide improved absorbent structures comprising certain types of blown microfibers, crimped synthetic staple fibers and a fluid control system to handle the aqueous body fluids which such structures are to imbibe.

It is a further object of the present invention to provide absorbent structures which have especially desirable fluid acquisition, distribution and storage characteristics but which are also exceptionally resistant to tearing and bunching, and which are especially flexible and resilient.

It is a further object of the present invention to provide disposable absorbent articles such as sanitary napkins, diapers, training pants, incontinence pads and the like which utilize such improved absorbent structures to form their absorbent cores.

SUMMARY OF THE INVENTION

The present invention is directed to a certain type of absorbent composite structure suitable for use in disposable absorbent articles of improved comfort, integrity and fluid handling characteristics. Such composite structures comprise (a) from about 10% to 85% by weight of blown microfibers, (b) from about 10% to 85% by weight of substantially nonabsorbent synthetic staple fibers, (c) from about 1% to 60% by weight of a fluid control system in particle form, and (d) from about 0.1% to 10% by weight of a hydrophilizing agent.

The blown microfibers essentially present in such structures can range in diameter between about 1 and 50 microns. The nonabsorbent staple fibers can have a denier varying between about 5 and 70 and a percent crimp of at least about 15%. Both microfibers and staple fibers are formed from synthetic polymeric material having a modulus value, when dry, of at least about $0.1 \times 10^{10}$ dynes/cm$^2$. The modulus value of both the microfiber polymer and the staple fiber polymer should not significantly diminish when these fibers are wetted. Microfibers and staple fibers are preferably present in such structures in amounts such that the weight ratio of the microfiber component to the staple fiber component ranges from about 1:3 to 3:1.

The fluid control system essentially comprises nongelling, hydrophilic particulate entities, substantially all of which have a greatest dimension ranging from about 0.01 mm to 10 mm. These nongelling hydrophilic particulate entities must also have a ratio of greatest dimension to smallest dimension of about 10:1 or less. Optionally, but preferably, the fluid control system will also comprise nonfibrous particles of hydrogel-forming polymeric gelling agent. If present, these polymeric gelling agent particles should range in size between about 10 microns and 2 mm. The polymeric gelling agent should have an equilibrium gel volume of at least about 20 g of artificial menses per gram of gelling agent and an extractable polymer content of no more than about 17% by weight in synthetic urine. If utilized in the fluid control system, polymeric gelling agent particles are present such that the weight ratio of nongelling hydrophilic particulate entities to polymeric gelling agent ranges from about 5:1 to 1:5.

In the composite structures of the present invention, the microfiber, staple fiber and fluid control system particles are combined, generally in a substantially unbonded manner, such that the resulting composite web has a dry density of from about 0.006 to 0.10 gram per cm$^3$. Preferably such a web will be formed into a structure having longitudinal, transverse and thickness dimensions. Such webs will generally exhibit both wet and dry resilience properties which enable such a composite web to recover to a dimension which is at least 50% of its original transverse dimension after being compressed to a transverse dimension which is 40% of its original transverse dimension.

BRIEF DESCRIPTION OF THE DRAWINGS

FIG. 3 represents a cut-away view of a sanitary napkin which employs a composite absorbent structure of this invention as an absorbent core.

FIG. 4 represents a cut-away view of a disposable diaper which employs a composite absorbent structure of this invention as an absorbent core.

FIG. 5 represents a cut-away view of a disposable training pants product which employs a composite absorbent structure of this invention as an absorbent core.

DETAILED DESCRIPTION OF THE INVENTION

Figure 1:
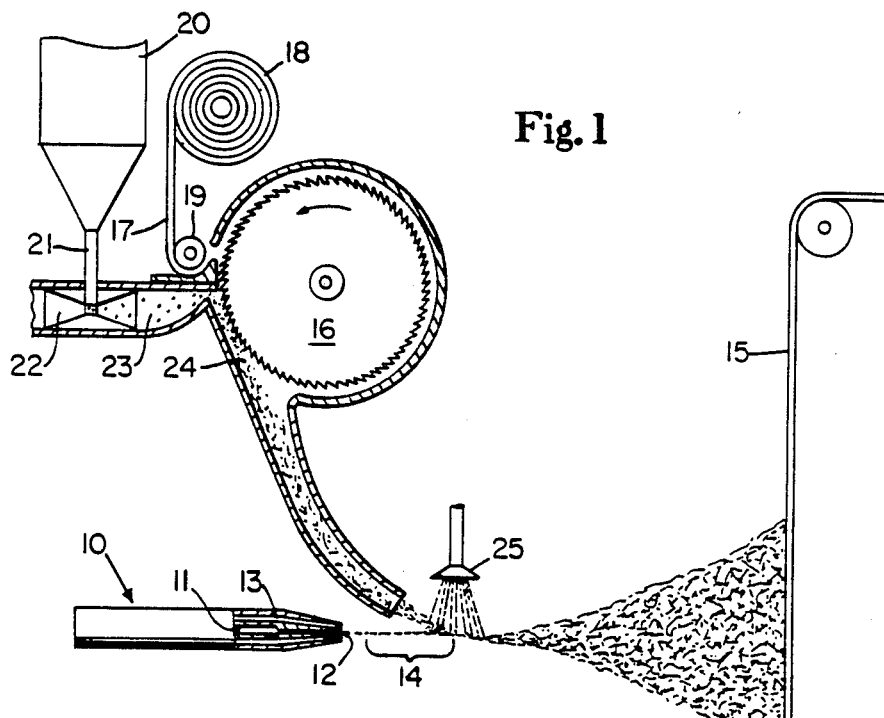
FIG. 1 is a schematic diagram of apparatus used in preparing the composite absorbent structures of this invention.

The absorbent structures of the present invention are composites which contain both fibrous and nonfibrous components. For purposes of this invention, the terms "fibers" and "fibrous" refer to a specific type of "particulate" material wherein the length to diameter ratio of such particulate material is greater than about 10. "Nonfibrous" particles, conversely, are those wherein the length to diameter ratio is about 10 or less.

One essential fibrous component of the composite absorbent structure herein comprises blown microfibers formed from synthetic polymeric material that provides fibers of particular size and stiffness characteristics. Blown microfibers are very fine fibers prepared by extruding liquified, fiber-forming polymer through orifices in a die into a high velocity gaseous stream. Fibers are attenuated by the gaseous stream and are subsequently solidified. The resulting stream of solidified fibers can be collected, e.g., on a screen disposed in the gaseous stream, as an entangled coherent fibrous mass. Such an entangled fibrous mass is characterized by extreme entanglement of the microfibers. This entanglement provides coherency and strength to the resulting web structure and also adapts the composite web structure to contain the staple fibers and retain the particulate fluid control system within the structure. The microfibers are entangled sufficiently that it is generally impossible to remove one complete microfiber from the mass of microfibers or to trace one microfiber from beginning to end. The theoretical aspect ratio (ratio of length to diameter) of blown microfibers in the web structures herein approaches infinity, although significant discontinuity of the microfibers can occur during composite preparation.

Blown microfibers useful herein may be either melt-blown or solution-blown. Melt-blown fibers are those which are liquified by heating the desired fiber-forming polymeric material in order to form the extruded microfibers. Melt-blown fibers are preferred for use in forming the composite structures of the present invention. However, solution-blown fibers in which the fiber-forming material is liquified by inclusion of a volatile solvent, can also be used. Carey, Jr., U.S. Pat. No. 4,011,067, Issued Mar. 8, 1977 incorporated herein by reference, discloses apparatus and procedures for preparing webs of blown microfibers. Microfibers will frequently be generally cylindrical in shape but other fiber geometries are also possible, e.g., wherein cross-sections of microfibers are elliptical, rectangular, triangular, etc.

The blown microfibers which form an essential component of the composite absorbent structures herein must have certain size and stiffness characteristics in order to impart the requisite flexibility, integrity and resilience features to such absorbent structures. In particular, substantially all of the individual blown microfibers included in the structures herein should have a diameter less than about 50 microns. More preferably the microfibers will have an average diameter ranging from about 1 to 10 microns. For purposes of the present invention, microfiber diameter can be determined from microfiber cross-sectional area, calculated by assuming that such cross-sectional area is circular.

The microfibers utilized should also meet certain stiffness requirements. Microfiber stiffness is a function of both fiber geometry and the type of polymeric material used to form the microfiber. For purposes of the present invention, microfiber stiffness can be quantified by specifying a modulus value for the microfiber polymer material along with fiber geometry and size as hereinbefore described. The modulus of the microfiber polymer material, e.g., the modulus of elasticity or tensile modulus, is in general defined as the ratio of change in stress to change in strain when a given amount of strain is imposed on a sample of polymeric material. Thus this modulus is usually characterized as a slope of the initial portion of the stress versus strain curve when strain is plotted as a function of applied stress for a given piece of polymeric material.

Determination of the modulus of the microfiber polymer material can be carried out in a variety of ways on materials in fiber form as outlined in the *Handbook of Physical and Mechanical Testing for Paper and Paperboard*, Vol. 1; Richard E. Mark, Editor; Marcel Dekker, Inc.; 1983, pp 447–456 and p 465, incorporated herein by reference. Measurements of imposed strain and the resulting stress response can be carried out using, for example, Instron or Dynamic Mechanical Analyzer apparatus. Modulus determinations do not need to be carried out on materials which are actually in fiber form. Indeed, direct measurement of modulus by testing of individual microfibers is not necessary. Instead, modulus values can and frequently are determined by testing polymeric materials in any convenient configuration, e.g., larger fibers, strips, pellets, etc.

For purposes of the present invention, modulus values for the microfiber material are determined at room temperature, i.e., at 20° C. Microfibers useful herein are those which are prepared from polymers that have modulus values of at least about $0.1 \times 10^{10}$ dynes/cm$^2$, more preferably from about $0.5 \times 10^{10}$ to $3.5 \times 10^{10}$ dynes/cm$^2$. Generally the polymeric material used to form such microfibers is, in and of itself, relatively nonabsorbent. Thus the modulus value for the microfiber material will generally fall within the foregoing ranges whether the microfibers are wet or dry. It is, in fact, essential that the modulus of the microfiber material not diminish significantly when the microfibers are wetted. For purposes of this invention, this means that the modulus of the microfiber material when wet should be at least about 70% of the modulus of the dry material, more preferably at least 80% of the dry modulus value. Such microfiber material is considered as wetted after it has been soaked, i.e., saturated with menstrual fluid or synthetic urine.

In order to realize microfibers of the required size and stiffness, the microfibers useful in the structures herein can be prepared from a synthetic polymer material which has a melting point of from about 100° C. to 265° C. and which will provide microfibers of the requisite diameter. Synthetic polymer materials having such characteristics include, for example, polyolefins, polyesters, polyamides, polyacrylics and polystyrenes. Specific examples of suitable polymeric material include polypropylene, polyethylene, polyethylene terephthalate (PET) and nylon. Polypropylene is highly preferred.

The blown microfiber component of the composite structures herein will generally comprise from about 10% to 85% by weight of the dry composite structure. More preferably, the microfiber component should comprise from about 20% to 65% by weight of the dry composite. For composite structures especially suitable for use in sanitary napkins, the microfiber component preferably comprises from about 25% to 50% by weight of the dry composite structure. For composite structures especially suitable for use in infant diapers, the microfiber component preferably comprises from about 25% to 65% by weight of the dry composite structure. For composite structures especially suitable for use in disposable training pants, the microfiber component preferably comprises from about 25% to 65% by weight of the dry composite structure. As discussed more fully hereinafter, the amount of microfiber component employed relative to the amount of staple fiber can also be important to the realization of composite structures of especially desirable comfort and fluid handling properties.

A second essential fibrous component of the composite absorbent structures herein comprises substantially nonabsorbent, crimped, synthetic staple fibers. The staple fibers, when combined with the microfibers as hereinafter described, serve to impart desirable bulk, fluid acquisition characteristics and resilience properties to the composite absorbent structures of this invention. Substantially all of the staple fibers incorporated into the absorbent structures herein will preferably range in length from about 0.1 to 15 cm, more preferably from about 2 to 7 cm.

The individual staple fibers used in the compositions herein are in and of themselves substantially nonabsorbent. Thus, such fibers must be prepared from synthetic polymer material which does not substantially swell or gel in the presence of fluids (e.g., urine, menses) encountered in disposable absorbent products. Accordingly, the synthetic staple fibers of the present invention, unlike the staple fibers used in several types of prior art absorbent webs, must have a water retention value (WRV) of less than about 15%, more preferably less than about 10% and even more preferably less than 5%. The water retention value is a measure of the amount of water absorbed by the staple fibers themselves; determination of WRVs for purposes of this invention is described in greater detail hereinafter. The absorbent structures of the present invention are preferably substantially free of absorbent staple fibers, e.g., cotton, rayon, cellulose, etc., which have WRV values of 15% or greater.

Suitable polymeric materials which do provide substantially nonabsorbent fibers of the requisite WRV include polyesters, polyolefins, polyacrylics, polyamides, polystyrenes and the like. In particular, staple fibers made of polyethylene, polypropylene and polyethylene terephthalate (PET, i.e., "Dacron") are especially preferred.

The staple fibers used in the absorbent structures of this invention must be crimped in order for the resulting absorbent structures to have the requisite resilience and resistance to bunching during use in absorbent products. Crimped fibers are those which have a continuous wavy, curvy or jagged character along their length. Fiber crimping of this type is described more fully in Hauser; U.S. Pat. No. 4,118,531; Issued Oct. 3, 1978, incorporated herein by reference. As noted in this '531 patent, crimped fibers of this type, which contribute to the desirable properties of absorbent structures containing them, are those which have a crimp count of at least two crimps per centimeter and a percent crimp of at least about 15%, preferably at least about 25%. Percent crimp is defined as the difference between the uncrimped length of the fiber (measured after fully straightening a sample fiber) and the crimped length (measured by suspending the sample fiber with a weight attached to one end equal to 2 mg. per decitex of the fiber, which straightens the large-radius bends of the fiber) divided by the crimped length and multiplied by 100.

The crimped synthetic staple fibers of the absorbent structures herein will generally have a denier ranging from about 5 to 70. More preferably the denier of the staple fibers will range between about 10 and 25.

In addition to particular size and crimping characteristics, the staple fibers of the structures of the present invention must also have certain stiffness characteristics. As with the microfibers used, staple fiber stiffness is a function of both fiber geometry and type of polymer material used to form the fiber. For purposes of the present invention, staple fiber stiffness, like stiffness of the microfibers used, can be quantified by specifying a fiber material modulus value along with fiber geometry and fiber size as hereinbefore described. The modulus value for material used to form staple fibers is defined in the same manner as the modulus value for the microfiber material as hereinbefore discussed. The staple fiber material used in the present invention will generally have a modulus value of at least about $0.1 \times 10^{10}$ dynes/cm$^2$, more preferably from about $2.5 \times 10^{10}$ to $3.5 \times 10^{10}$ dynes/cm$^2$. As with the microfibers employed, the substantially nonabsorbent nature of the staple fibers means that there should be little significant difference in modulus of the staple fiber material whether the staple fiber material is wet or dry when the modulus is determined. Accordingly, the modulus value, both wet and dry, must fall within the ranges hereinbefore set forth for the staple fiber material. Furthermore, as with the microfiber material modulus, the modulus value of the dry staple fiber material must not significantly diminish when the staple fiber material is wetted.

Both the actual amount of staple fiber incorporated into the absorbent web structures of the present invention, as well as the amount of staple fibers relative to the microfiber component in such structures, can affect the fluid handling, integrity, resilience and comfort properties of the resulting composite absorbent webs. Generally, the staple fiber component can comprise from about 10% to 85% by weight of the dry absorbent composite structures herein, more preferably from about 20% to 60% by weight of the dry composite structures. For composite structures especially suitable for use in sanitary napkins, the staple fiber component should comprise from about 20% to 50% by weight of the dry composite. For composite structures especially suitable for use in infant diapers, the staple fiber component preferably comprises from about 10% to 50% by weight of the dry composite. For composite structures especially suitable for use in disposable training pants, the staple fiber component will preferably comprise from about 10% to 50% by weight of the dry composite. The weight ratio of microfiber to staple fiber in such structures will preferably range from about 1:3 to 3:1, more preferably from about 3:7 to 7:3.

A third essential element of the composite absorbent structures herein comprises a certain type of particle-form, i.e., nonfibrous, fluid control system. Such a fluid control system essentially comprises nongelling, hydrophilic particulate entities and optionally also comprises hydrogel-forming polymeric gelling agent particles. This fluid control system serves to effectively manage discharged body fluids which are brought into contact with the composite absorbent structures herein. In particular, the fluid control system facilitates the acquisition or uptake of fluid striking the surface of the composite structure and then serves to distribute such fluid rapidly and efficiently to more remote areas of the composite structure. Ultimately, preferred two-component fluid control systems also serve to hold acquired fluid in a gelled, immobilized state within the composite structure interstices. It has been discovered that the particular type of fluid control system used in this invention is especially effective in managing fluid in these ways. Most importantly, this type of system does so without adversely affecting the flexibility and resiliency properties of the particular composite structures in which it is employed.

The essential component of the fluid control system of the composite structures herein comprises hydrophilic particulate entities which facilitate the transport of body fluid and which may swell in doing so but which do not form gels upon imbibing such fluid. For purposes of the present invention, an entity is "hydrophilic" if water or aqueous body fluid readily spreads on or over the surface of the entity (without regard to whether or not the entity actually imbibes fluid or forms a gel). Furthermore, for purposes of this invention, a hydrophilic entity is nongelling if, even upon prolonged contact with aqueous body fluids, it does not form a viscous, jelly-like material. Nongelling absorbents of this type can furthermore be characterized as those whose fluid absorbent characteristics are not dependent upon electrolyte content of the fluid being absorbed and are also less susceptible to the negative effect of body fluid solids on fluid transport. It is believed that these hydrophilic entities serve to enhance fluid transport through the composite structures herein by providing increased capillarity within the web structures. The hydrophilic particulate entities should, of course, be substantially insoluble in aqueous body fluids.

The most important feature of the nongelling hydrophilic particulate entities used in the fluid control system is their size and geometric configuration. In particular, these entities should have a greatest dimension ranging from about 0.01 to about 10 mm, more preferably from about 0.02 to 0.5 mm. Furthermore, such entities must not have a greatest dimension to smallest dimension ratio (aspect ratio) which exceeds about 10. The aspect ratio of the hydrophilic entities will preferably be 5 or less. Particulate entities within these size and shape specifications are especially useful because entities of this particular configuration appear to significantly enhance fluid transport within and throughout the composite absorbent structures herein. At the same time, entities of these size and shape specifications do not significantly interfere with the desirable resilience and flexibility characteristics of the composite absorbent structures.

Within the foregoing size and geometric shape constraints, the hydrophilic particulate entities used in the fluid control system can be prepared from any material which is nongelling and hydrophilic. For purposes of this invention, an entity is considered to be hydrophilic even if it has been fashioned from hydrophobic material but has been subsequently rendered hydrophilic by treatment with a hydrophilizing agent, e.g., surfactant, as hereinafter more fully described. Suitable types of hydrophilic entity material thus include cellulose, cellulose derivatives, polyolefins such as polyethylene and polypropylene, polyacrylics, polyesters, polyamides, polystyrenes, polyurethanes, clay, kaolin, talc, calcium carbonate, sodium sulfate, sodium carbonate and aluminum oxide.

Materials of the foregoing types can be fashioned into the nongelling hydrophilic particulate entities used in this invention by mechanical working to ensure that the requisite size and shape parameters are met. Frequently such materials will be formed initially into fibers, flakes, sheets, films, foams, webs, etc. which will need to be chopped, torn apart, ground, powdered, twisted, knotted or otherwise finely divided in order to form particulate entities of the requisite size and geometric shape configuration.

The nongelling hydrophilic particulate entities used in the fluid control system may be porous or substantially nonporous. Porous, and hence relatively absorptive, hydrophilic entities are preferred. Porosity of the hydrophilic entity material may arise by virtue of the nature of the hydrophilic entity material selected or by virtue of the manner in which the hydrophilic entities are prepared.

One manner of preparing porous hydrophilic entities includes the creation of porosity by forming small bundles of microfibers into discrete particle-like entities, i.e., microwebs. Such microfiber microwebs have a dense nucleus with individual fibers and/or fiber bundles protruding therefrom. The nuclei preferably have an average diameter of about 0.05 to 4 mm, more preferably 0.2 to 2 mm, and the fibers and/or fiber bundles preferably extend from the nuclei to provide an overall diameter of about 0.07 to 10 mm, more preferably about 0.1 to 5 mm.

Microfiber microwebs of the foregoing type can be produced by forming a microfiber source web and divellicating, or tearing apart, the microfiber source web. The microfiber source web is preferably melt blown from a thermoplastic fiber-forming material as described in Wente, Van A. et al, "Superfine Thermoplasic Fibers," *Industrial Engineering Chemistry*, Vol. 48, pp. 1342–1346, with the fibers having a diameter of less than about 10 microns. The divellication of the microfiber source web is preferably accomplished by subjecting the microfiber source web to the action of a lickerin, i.e., a toothed-roll. The teeth of the lickerin protrude from the surface thereof at a sufficiently low angle, preferably less than about 60°, more preferably less than about 40°, to produce the microwebs having dense nuclei and fibers and/or fiber bundles protruding from the nuclei.

Another type of porous hydrophilic entity which may be useful in the composite web structures are the "fibrids" described in Parrish et al; U.S. Pat. No. 2,988,782; Issued June 20, 1986, which patent is incorporated herein by reference. Those fibrids which have the size and shape characteristics set forth hereinbefore and which are or have been rendered hydrophilic can be used as the nongelling hydrophilic particulate entities in the absorbent structures herein. However, based on their structure, such fibrids are probably less sorbent than the hereinbefore described microfiber microwebs.

Porous hydrophilic entities may also be prepared by fashioning the hydrophilic entities from a naturally occurring or synthetically produced porous material. Thus, materials such as foams or sponges can be employed as hydrophilic particulate entities provided such foams or sponges are finely divided into entities within the size and shape configurations hereinbefore specified. Especially preferred materials of this type include the shredded particles of hydrophilic polyurethane foam described in Isgur et al; U.S. Pat. No. 4,110,508; Issued Aug. 29, 1978, incorporated herein by reference. Other preferred porous materials include finely divided particles of cellulose sponge, e.g., fine porous sponges of regenerated cellulose.

Of all the foregoing types of materials which may be used to form the hydrophilic particulate entity component of the fluid control systems herein, the most preferred is powdered cellulose having an average greatest dimension ranging from about 0.05 to about 0.3 mm and an average aspect ratio of 5 or less. Powdered cellulose material of this type is commercially available and is marketed, for example, under the trade name SOLKA-FLOC by the James River Corporation.

An optional, but highly preferred, component of the fluid control systems which can be used in the composite structures herein comprises nonfibrous particles of a specific type of hydrogel-forming polymeric gelling agent. These polymeric gelling agents are those materials which, upon contact with fluids (i.e., liquids) such as water or body fluids, imbibe such fluids and thereby form hydrogels. In this manner, fluid discharged into the absorbent structures herein can be acquired and held by the particles of the polymeric gelling agent, thereby providing the structures herein with enhanced absorbent capacity.

The polymeric gelling agent particles which may be used in the fluid control system will generally comprise a substantially water-insoluble, slightly cross-linked, partially neutralized, hydrogel-forming polymer material. Such polymer materials can be prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Suitable unsaturated acidic monomers for use in preparing the polymeric gelling agents used in this instance include those listed in Brandt/Goldman/Inglin; U.S. Pat. No. 4,654,039, Issued Mar. 31, 1987, incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agents optionally used in the fluid control system, the polymeric component formed from unsaturated, acid-containing monomers may be grafted on to other types of polymer moieties such as starch or cellulose. Acrylic acid grafted starch materials of this type are especially preferred for use herein.

Preferred polymer gelling agents which can be prepared from conventional types of monomers include hydrolyzed acrylonitrile grafted starch, acrylic acid grafted starch, polyacrylates, isobutylene maleic anhydride copolymers and combinations thereof. Especially preferred are the polyacrylates and acrylic acid grafted starch.

Whatever the nature of the basic polymer components of the hydrogel-forming polymeric gelling agents optionally used in the fluid control system, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in Masuda et al; U.S. Pat. No. 4,076,663; Issued Feb. 28, 1978, incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5 mole percent of the resulting hydrogel-forming polymer material. More preferably, the cross-linking agent will comprise from about 0.01 mole percent to 3 mole percent of the hydrogel-forming polymeric gelling agent used herein.

The slightly cross-linked, hydrogel-forming polymeric gelling agents which may be used in the fluid control system of the present invention are generally employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation.

Suitable salt-forming cations include alkali metal, ammonium, substituted ammonium and amines. This percentage of the total monomers utilized which are neutralized acid group-containing monomers is referred to herein as the "degree of neutralization."

The polymeric gelling agent materials optionally used in the fluid control system herein will also have a relatively high capacity for imbibing fluids encountered in absorbent structures and preferably will also imbibe such fluid at a relatively fast rate. Both of these characteristics, capacity and uptake rate, can be quantified by referencing the "gel volume" of the polymeric gelling agents which are to be selected for use in the present invention.

For purposes of this invention, gel volume can be defined in terms of the amount of artificial menses absorbed by any given polymeric gelling agent and is specified as grams of artificial menses per gram of polymeric gelling agent in a procedure hereinafter defined. The artificial menses used to define gel volume herein is a mixture of sheep's blood and a synthetic mucous component. The preparation of artificial menses which can be used in making gel volume determinations is set forth hereinafter in the Test Methods section.

Gel volume can be determined by swelling samples of particles of polymeric gelling agent to be tested with artificial menses fluid. Samples of polymeric gelling agent are maintained in contact with the swelling fluid at ambient temperature for about one hour so that swelling equilibrium is attained. The swollen gel samples are then centrifuged to remove fluid not actually imbibed by the polymeric gelling agent. Using a procedure described in greater detail hereinafter in the Test Methods section, the gel volume of the polymeric gelling agent in grams of artificial menses per gram of polymeric gelling agent can then be calculated from experimentally determined measurements.

The polymeric gelling agent materials useful in the fluid control systems of the present invention are those which have an equilibrium (1 hour) gel volume of at least about 20 grams of artificial menses per gram of polymeric gelling agent. More preferably, the polymeric gelling agent materials which are useful have an equilibrium (1 hour) gel volume of from about 25 to 50 grams of artificial menses per gram of polymeric gelling agent. Polymeric gelling agent material having such relatively high gel volume characteristics are especially useful in absorbent structures herein since the hydrogels formed from such materials can, by definition, hold desirably high amounts of discharged body fluids such as menses and urine.

When the absorbent composite structures herein are to be used in infant diapers, adult incontinence products or training pants, the gel volume of the polymeric gelling agents employed in such structures can, and frequently will, be expressed in terms of grams of synthetic urine per gram of polymeric gelling agent instead of grams of artificial menses per gram of polymeric gelling agent. Gel volume in synthetic urine can be determined by forming a suspension of about 0.1-0.2 parts of dried polymeric gelling agent to be tested with about 20 parts of this synthetic urine. This suspension is maintained at ambient temperature under gentle stirring for about 1 hour so that swelling equilibrium is attained. Using a procedure described in greater detail hereinafter in the Test Methods section, the gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension. The structures of the present invention which are to be used in diapers, adult incontinence products or training pants will generally employ polymeric gelling agents having a gel volume of from about 20 to 70 grams, more preferably from about 30 to 60 grams, of synthetic urine per gram of polymeric gelling agent.

In addition to their relatively high equilibrium (1 hour) gel volume, the hydrogels formed from the polymeric gelling agents used in the present invention preferably also will be able to acquire and tie up fluid quickly. For this reason, the polymeric gelling agent materials useful herein preferably also have certain gel volume values after two minutes of fluid contact in addition to having the particular equilibrium, i.e., one hour, gel volume values specified hereinbefore. In particular, the polymeric gelling agents useful herein will generally have a two minute gel volume which is at least 40% of the equilibrium (1 hour) gel volume. More preferably the two-minute gel volume for the polymeric gelling agents herein will be at least 50% of the equilibrium (1 hour) gel volume.

Another feature of the polymeric gelling agents which are useful as an optional component of the fluid control system of the absorbent structures herein relates to the level of extractable polymer material present in such hydrogel-forming material. Extractable polymer levels can be determined by contacting a sample of hydrogel-forming polymeric gelling agent material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. Synthetic urine is utilized in such a procedure since extractable polymer content in synthetic urine is more readily determined than extractable polymer content in artificial menses. The particular procedure used to determine extractable polymer content of the polymeric gelling agents used herein is set forth in Brandt, Goldman and Inglin; U.S. Pat. No. 4,654,039; Issued Mar. 31, 1987, incorporated herein by reference. Polymeric gelling agent materials especially useful in the fluid control systems herein are those which have an equilibrium extractables content in synthetic urine of no more than about 17%, preferably no more than about 10% by weight of the polymeric gelling agent.

The polymeric gelling agent materials hereinbefore described, when utilized in the fluid control system of the absorbent structures herein, are employed in the form of discrete particles. Such polymeric gelling agent particles can be of any desired shape, e.g., spherical or semi-spherical, cubic, rod-like polyhedral, etc. Shapes having a large greatest dimension/smallest dimension ratio, like flakes are also contemplated for use herein, provided the greatest dimension/smallest dimension ratio does not exceed 10. Preferably this ratio will not exceed 6. Agglomerates of polymeric gelling agent particles may also be used.

Although the absorbent structures herein are expected to perform well with polymeric gelling agent particles having a particle size varying over a wide range, other considerations may preclude the use of very small or very large particles. For reasons of industrial hygiene, average particle sizes smaller than about 10 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use in the fluid control systems herein are polymeric gelling agent particles substantially all of which have a particle size of from about 10 microns to about 2 mm. "Particle Size" as used herein means the smallest dimension of the individual particles.

When the fluid control system comprises both nongelling hydrophilic entities and polymeric gelling agent, these two types of particles need not be associated with each other in any specific manner other than by being incorporated into the same absorbent composite structure. On the other hand, it may be convenient to combine or premix the polymeric gelling agent and the nongelling hydrophilic particulate entities prior to incorporating the resulting fluid control system into the composite structures as a particulate mixture.

Polymeric gelling agent particles and the nongelling hydrophilic particulate entities may also be more intimately associated than by simply being in admixture with each other. For example, gelling agents and nongelling hydrophilic entity particles may be agglomerated together so long as each type of particle in the agglomerate retains its requisite identity, size and geometric configuration. In another embodiment, polymeric gelling agent and nongelling hydrophilic entities may be associated with each other in individual particles in a core-shell arrangement with the gelling agent as the core surrounded by a nongelling hydrophilic shell. Particles of this type include microfiber microwebs which can be prepared, for example, by divellicating a microfiber source web which has dispersed therein the polymeric gelling agent particles. Source webs of this type include those which are described, for example, in Kolpin/Brownlee, U.S. Pat. No. 4,429,001, Issued Jan. 31, 1984, which patent is incorporated herein by reference. Particles formed in this manner have a dense nucleus of the polymeric gelling agent particles and entangled microfibers with the nucleus being surrounded by a mass or bundle of entangled microfibers.

Within the composite web structures herein, the particles of the fluid control system may or may not be uniformly distributed. In particular, there may be regions or zones of the composite web structures which have higher concentrations of fluid control system particles than do other regions or zones of the structure. Furthermore, there may be regions or zones of the composite structures herein wherein the concentration of nongelling hydrophilic entities is higher than that of polymeric gelling or vice versa. In one embodiment of this type, there may be a concentration gradient of nongelling hydrophilic entities along the thickness dimension of the composite structure with the highest concentration of hydrophilic entities being at or near the surface of the structure which receives fluid and the lowest concentration of hydrophilic entities being at or near the opposite end of the thickness dimension. In the same structure, the thickness dimension concentration gradient of the polymeric gelling agent may be of the opposite type wherein gelling agent concentration is greatest at or near the surface of the structure which does not receive the initial contact with fluid. In another embodiment, there may be a uniform concentration of hydrophilic entities along the thickness dimension of the structure with a concentration gradient of polymeric gelling agent along this dimension.

No matter how the nongelling hydrophilic particulate entities and polymeric gelling agent particles may be associated with each other or distributed within the fluid control system, when both components are present in the fluid control system, the overall weight ratio of the nongelling hydrophilic entities to the gelling agent will generally range from about 5:1 o 1:5. More preferably, the weight ratio of the nongelling hydrophilic entity component to the gelling agent component will range from about 4:1 to 1:1.

The fluid control system as hereinbefore described should be incorporated into the composite absorbent structures herein in a concentration which is sufficient to effect the desired degree of fluid management within the structure. Thus, the fluid control system will generally be present in the composite structures herein to the extent of from about 1% to 60% by weight of the structure. More preferably, the fluid control system will comprise from about 15% to 55% by weight of the structure. For composite structures especially suitable for use in sanitary napkins, the fluid control system should comprise from about 20% to 50% by weight of the dry composite. For composite structures especially suitable for use in infant diapers, the fluid control system should comprise from about 20% to 55% by weight of the dry composite. For composite structures especially suitable for use in disposable training pants, the fluid control system preferably comprises from about 20% to 55% by weight of the dry composite.

A fourth essential element of the absorbent structures herein is a hydrophilizing agent which can be applied to the synthetic microfiber, staple fiber and fluid control system components to enhance the wettability of these fibers and particulate materials. Materials of this type are well-known in the art and can comprise, for example, surfactant materials or colloidal silica. If a surfactant is employed as the hydrophilizing agent, the type of surfactant can be anionic, cationic or nonionic with nonionic materials being especially preferred. Suitable nonionic surfactants include the ethoxylated alcohols and ethoxylated alkylphenols.

The hydrophilizing agent, in either solid or liquid form, can be applied to the synthetic microfibers, staple fibers and/or fluid control system components of the absorbent structures herein at any convenient stage before, during or after preparation of such structures. Thus the hydrophilizing agent may be applied to the microfibers, staple fibers and/or fluid control systems before they are comingled to form the absorbent web structures herein. Alternatively, the hydrophilizing agent may be added to the comingled mass of microfibers, staple fibers and/or fluid control system components used in forming the absorbent web structures herein. Hydrophilizing agent may furthermore be compounded with the microfiber-forming material before the microfibers are formed.

Hydrophilizing agent may also be applied to the web structures after such structures have been formed, for example, by spraying liquid, nonaqueous, nonionic surfactant onto the formed web structures. No matter how or when hydrophilizing agent is incorporated into the structures herein, hydrophilizing agent will generally comprise from about 0.01% to 10% by weight of the finished absorbent web structures, more preferably from about 0.01% to 5% by weight of such structures.

The absorbent web structures of the present invention can be prepared by forming a gaseous e.g., air, stream which comprises the blown microfiber, staple fiber, particulate fluid control system and hydrophilizing agent components, and by conveying this fiber and particle-containing stream to a collector device wherein an entangled mass of fibers and particles is air-laid as a continuous fibrous web. Apparatus for carrying out such a process can include conventional fiber blowing structures as taught, for example, in Wente, "Superfine Thermoplastic Fibers", *Industrial Engineering Chemistry, Vol.* 48, pages 1342 et seq (1956), or in Report No. 4364 of the Naval Research Laboratories, published May 25, 1954, entitled "Manufacture of Superfine Organic Fibers" by Wente et al. These publications are incorporated herein by reference.

Typical apparatus for preparing melt blown microfiber-based web structures of the present invention is schematically illustrated in FIG. 1 of the drawings submitted herewith. The apparatus of FIG. 1 includes a die, 10, which has an extrusion chamber, 11, through which liquified microfiber-forming material is advanced; die orifices, 12, arranged in line across the forward end of the die and through which the microfiber-forming material is extruded; and cooperating gas orifices, 13, through which a gas, typically heated air, is forced at very high velocity. The high-velocity gaseous stream draws out and attenuates the extruded microfiber-forming material, whereupon the microfiber-forming material solidifies as microfibers during travel through region, 14, to a collector, 15. The collector, 15, is typically a finely perforated screen, which in this case is in the form of a closed-loop belt, but which can take alternative forms, such as a flat screen or a drum or cylinder. Gas-withdrawal apparatus may be positioned behind the screen to assist in deposition of fibers and removal of gas. Alternatively, two dies may be used and arranged so that the streams of melt blown microfibers issuing from them intersect to form one stream that continues to a collector, 15.

The apparatus shown in FIG. 1 also includes means for introducing the fluid control system particles and nonabsorbent staple fibers into the absorbent composite structures of the present invention. The staple fibers are introduced into the stream of melt blown microfibers through the use of a lickerin roll, 16. A web, 17, of crimped staple fibers, typically a loose, nonwoven web such as prepared on a garnet machine or "Rando-Weber", is supplied from a supply roll, 18, under a drive roll, 19, where the leading edge engages against the lickerin roll, 16. The lickerin roll, 16, turns in the direction of the arrow and picks the crimped staple fibers from the leading edge of the web, 17, dissociating the crimped staple fibers from one another. The fluid control system particles are supplied from a particulate hopper, 20, containing, for example, a mixture of hydrophilic particulate entities and polymeric gelling agent particles. Alternatively, separate particle hoppers may be used to supply hydrophilic entities and polymeric gelling agent particles to the process at different rates or in different amounts. Particles from hopper, 20, are supplied through an inductor, 21, which meters the amount of particles flowing into a venturi, 22, which is in duct, 23. An air stream flows through duct, 23, for conveying the fluid control system particles. The particles are conveyed to inclined duct, 24, where the fluidized stream of particles becomes the carrier stream for the crimped staple fibers delivered by the lickerin roll, 16. The fluid control system particles and crimped staple fibers are conveyed in the air stream through inclined duct, 24, and into the stream of melt blown microfibers where the particles and crimped staple fibers become mixed with the melt blown microfibers. The mixed stream of melt blown microfibers, crimped staple fibers and fluid control system particles then continues to the collector, 15, where a web of randomly intermixed and intertangled microfibers, crimped staple fibers and fluid control system particles is formed. A spray jet, 25, may be used to apply the required hydrophilizing agent, e.g., a surfactant, to the mixed stream of blown microfibers, fluid control system particles and crimped staple fibers prior to collection at collector, 15.

The absorbent composite web structures prepared using such apparatus generally comprise intermingled or entangled masses of hydrophilized microfibers, crimped staple fibers and fluid control system particles. Such intermingled or entangled masses are substantially unbonded in the sense that they are substantially free of significant amounts of fibers and particles bonded to each other by chemical or fusion bonds. Thus, staple fibers and fluid control system particles should generally be combined with the microfiber stream after the microfibers have solidified to the point that substantially no interfiber or particle-fiber fusion bonds will be formed. Rather, the structural integrity of the composite web structures herein is generally maintained by the presence of mechanical or entanglement bonds throughout the structure.

Figure 2:
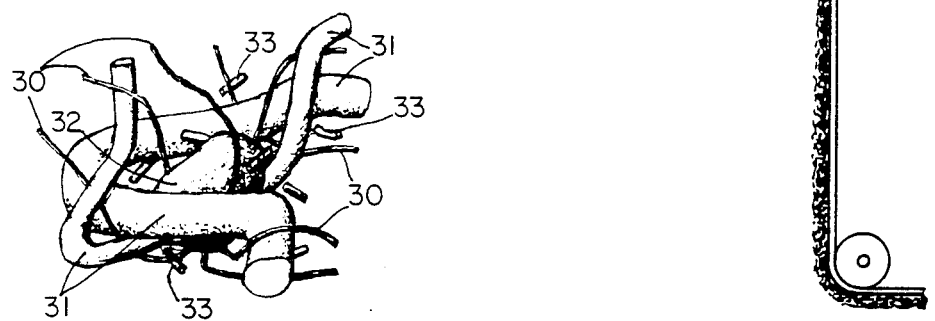
FIG. 2 is a greatly enlarged sectional representation of a portion of a preferred composite absorbent structure of this invention.

FIG. 2 of the drawing submitted herewith illustrates the general structural relationship of the microfiber, crimped staple fiber and fluid control system particle components in preferred composite webs of this invention. FIG. 2 shows entangled microfibers, 30, and crimped staple fibers, 31. The microfibers in particular entangle themselves with each other, with the staple fibers and with a particle of polymeric gelling agent, 32, and a hydrophilic particulate entity, 33, shown as, for example, a particle of powdered cellulose.

The composite web structures of the present invention can be made having a wide variety of properties depending upon the nature and the amounts of the web components employed, upon particular fiber orientation arrangements and upon the specific processing conditions utilized. For example, the absorbent web structures herein can be prepared having any desired basis weight. For use in disposable absorbent articles, dry basis weight of the web structures herein will preferably range from about 100 to 800 g/m$^2$, more preferably from about 100 to 500 g/m$^2$. When such structures are to be used as absorbent cores for sanitary napkins, dry basis weight will generally range from about 200 to 450 g/m$^2$. When structures are to be used in infant diapers, dry basis weight will generally range from about 100 to 700 gm/m$^2$. For disposable training pants, dry basis weight will generally range from about 100 to 700 gm/m$^2$.

Caliper of the absorbent web structures herein can also be widely varied depending upon the desired end use of the structures. Frequently caliper of the dry web structure will range from about 0.46 to 3.1 centimeters, more preferably from about 1.5 to 2.1 centimeters. The preferred web structures of the present invention, by virtue of both their density and the properties of their selected types of components, do not significantly expand, i.e., increase in caliper, upon imbibing body fluids and similar electrolytes (under conditions of minimal confining pressure i.e., a confining pressure of 0.005 kPa). The preferred webs herein, in fact, may actually decrease in caliper upon fluid acquisition. These unique fluid absorption characteristics of the web structures herein may in part be responsible for the especially desirable comfort properties which preferred absorbent structures of the present invention possess.

At a constant basis weight, variations in web structure caliper result in variations in density of the structures herein. For these absorbent structures, such web density and caliper variations can influence comfort response, response to compression (i.e., bending ability and resilience), absorbent response (i.e., capacity, fluid uptake rate and fluid binding tenacity) and the ability to maintain body contact for fluid acquisition. Web density and caliper can be adjusted, for example, by varying the distance from the microfiber extruder outlet to the collector, by changing the microfiber/staple fiber ratio, by altering the amount of fluid control system components employed, by changing the wind-up roll tension during web structure converting or by varying staple fiber denier and/or crimp level. The web structures of the present invention are those which have a dry density of from about 0.006 to 0.10 g/cm$^3$, more preferably from about 0.006 to 0.04 g/cm$^3$. For use as the absorbent core in sanitary napkin products, the web structures herein should generally have a density ranging from about 0.006 to 0.03 g/cm$^3$. For use in infant diapers, the web structures herein will generally have a density ranging from about 0.01 to 0.04 gm/cm$^3$. For use in disposable training pants, density of the structures herein will generally range from about 0.01 to 0.04 gm/cm$^3$.

Dry density, for purposes of the present invention, is measured under a confining pressure of about 0.0007 psi (0.005 kPa). Density of such structures need not be uniform throughout the structure. Within the density ranges hereinbefore set forth, structures of this invention can contain rebellions of relatively higher or relatively lower density.

In addition to their performance in accepting and holding discharged body fluids, another important feature of the composite web structures herein involves their wet and dry resilience properties. Resilience involves the propensity of the composite web structures herein to recover their original dimensions after being compressed. As noted hereinbefore, preferred composite web structures of this invention are those which exhibit both wet and dry resilience properties that enable a given three-dimensional composite web structure to recover to at least about 50%, and more preferably to at least about 65%, of its original transverse dimension after having been compressed to a transverse dimension which is 40% of its original transverse dimension. For purposes of this invention, such a determination of resilience can be made using a web structure of standard transverse dimension while embodying such a structure in a standard type of absorbent article chassis.

This standard chassis for determining web structure resilience is defined for purposes of this invention as the sanitary napkin of Example XIII hereinafter set forth. The standard "original" transverse dimension utilized is 6.35 cm (2.5 inches). Thus to determine resilience of the preferred composite web structures of this invention, web structure-containing sanitary pads of a given standard initial width (2.5 inches) can be compressed to the 60% strain level, i.e., to 1.0 inch in width, (40% of its original width), followed by removal of the compressive force to allow the sanitary pad to relax. Compressive force is applied for a period of three hours, followed by a relaxation period of 5 minutes. The final width of the pad is thereafter determined. Percent Resilience can then be calculated according to the equation:

$$\% \text{ Resilience} = \left[1 - \frac{(\text{Initial Width} - \text{Final Width})}{\text{Strain Level}}\right] \times 100$$

wherein Strain Level is the Initial pad width minus the Compressed Pad Width. The Percent Resilience according to this equation can be determined with the pads in either dry or wet condition.

The present invention also relates to disposable absorbent articles which utilize the absorbent composite structures herein as at least a portion of the fluid-absorbing "core" element. By "absorbent article" herein is meant a consumer product which is capable of absorbing significant quantities of water and other fluids (i.e., liquids), like body fluids. Examples of absorbent articles include disposable diapers, sanitary napkins, incontinence pads, disposable training pants, paper towels, facial tissues, and the like. These absorbent structures are particularly suitable for use in articles like sanitary napkins, diapers and incontinence pads.

Absorbent articles herein will frequently comprise a substantially liquid impervious backing sheet, a liquid pervious, relatively hydrophobic topsheet and an absorbent core comprising an absorbent structure of the present invention positioned between said backing sheet and said topsheet. Liquid impervious backing sheets can comprise any material, for example polyethylene or polypropylene having a caliper of about 1.5 mils, which will help retain fluid within the absorbent article. Relatively hydrophobic, liquid pervious topsheets can comprise any material such as polyester, polyolefin, rayon and the like which is substantially porous and permits a fluid to readily pass therethrough into the underlying absorbent core.

The absorbent core of disposable absorbent article embodiments of this invention can consist solely of one or more of the composite web structures herein. Alternatively, the absorbent core of such articles can comprise other conventional elements in addition to the composite web structures of the present invention. For example, absorbent articles herein may use a multilayer absorbent core configuration wherein a composite web structure of this invention is used in combination with one or more separate layers comprising conventional absorbent structures. Such conventional absorbent structures, for example, include air-laid webs of wood pulp or other cellulosic fibers, which webs may or may not contain particles or fibers of polymeric gelling agent of the same type as hereinafter described for use in the structures herein. Another type of conventional absorbent structure comprises a laminate of at least one layer of dispersed polymeric gelling agent particles, overwrapped with sheets of hydrophilic fiber material such as tissue paper. Laminate structures of this general type are described in Kramer, Young and Kock; U.S. Pat. No. 4,578,068; Issued Mar. 25, 1986, incorporated herein by reference.

One preferred type of absorbent article herein is one which utilizes a multi-layer absorbent core having a first layer, preferably a lower layer, comprising an air-laid web of cellulosic fibers containing from 0% to about 10% by weight of this cellulosic layer of polymer gelling agent and a second layer, preferably an upper layer, comprising a composite web structure of the present invention. Another preferred type of absorbent article herein utilizes a multi-layer absorbent core having an upper layer comprising a composite web structure of the present invention and an lower layer which comprises a laminate of at least one layer of dispersed particles of polymeric gelling agent overwrapped with sheets of tissue. For purposes of this invention, the upper layer of a multi-layer absorbent core is the layer closest to the body of the wearer, e.g., the layer closest to the article top sheet. The term lower layer conversely means the layer of a multi-layer absorbent core which is furthest away from the body of the wearer, e.g., the layer closest to the article backsheet.

As indicated hereinbefore, the fluid handling and comfort characteristics of the absorbent web structures herein render such structures especially suitable for use in absorbent articles in the form of sanitary napkins. Sanitary napkins (or in other terms, catamenial pads) utilizing the present absorbent structures may be derived from conventional sanitary napkins by simply replacing or supplementing the absorbent core thereof (typically a web of wood pulp fibers) with one or more absorbent composite structures of the present invention. In sanitary napkins, the composite structures herein may thus serve as a single layer absorbent core or may be utilized as one or more elements in a variety of multi-layered absorbent core arrangements as hereinbefore described.

An example of a typical sanitary napkin is shown in FIG. 3 of the drawings. This particular catamenial product comprises a pad, 40, of the absorbent composite structure of the present invention as a single layer absorbent core; a hydrophobic topsheet, 41; and a fluid impervious backsheet, 42. The topsheet and the backsheet are placed at opposite sides of the absorbent structure. Optionally, the absorbent structure is wrapped in envelope tissue, 43. Suitable materials for top sheets, bottom sheets and envelope tissue are well known in the art. A more detailed description of sanitary napkins and suitable materials for use therein is found in Duncan and Smith, U.S. Pat. Nos. 3,871,378, Issued Mar. 18, 1975; Mullane and Smith, 4,324,246, Issued Apr. 13, 1982 and Van Tillberg, 4,589,876, Issued May 20, 1986; the disclosures of which are incorporated herein by reference.

Other disposable absorbent articles which can employ the absorbent web structures herein are disposable diapers. Disposable diapers comprising the absorbent structures of the present invention may be made by using conventional diaper making techniques, but by replacing or supplementing the wood pulp fiber web ("airfelt") core which is typically used in conventional diapers with one or more composite web structures of the present invention. Composite web structures of this invention may thus be used in diapers in single layer or various multiple layer core configurations. Articles in the form of disposable diapers are fully described in Duncan and Baker, U.S. Pat. No. Re 26,151, Issued Jan. 31, 1967; Duncan, U.S. Pat. No. 3,592,194, Issued July 13, 1971; Duncan and Gellert, U.S. Pat. No. 3,489,148, Issued Jan. 13, 1970; and Buell, U.S. Pat. No. 3,860,003, Issued Jan. 14, 1975; which patents are incorporated herein by reference. A preferred disposable diaper for the purpose of this invention is illustrated by FIG. 4 of the drawings. Such a diaper includes an absorbent core, 50, comprising an absorbent composite structure of this invention; a topsheet, 51, superposed or co-extensive with one face of the core, and a liquid impervious backsheet, 52, superposed or coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another preferred type of absorbent article which can utilize the composite absorbent structures of the present invention comprises training pants. Such training pants will generally include a nonwoven, flexible substrate fashioned into a chassis in the form of briefs or shorts. An absorbent structure according to the present invention can then be affixed in the crotch area of such a chassis in order to serve as an absorbent "core." This absorbent core will frequently be overwrapped with envelope tissue or other liquid pervious, nonwoven material. Such core overwrapping thus serves as the "topsheet" for the training pants article.

The flexible substrate which forms the training pants chassis may comprise cloth or paper or other kinds of nonwoven substrate and may be elasticized or otherwise stretchable. Leg bands or waist bands of such training pants articles may be elasticized in conventional fashion to improve fit of the article. Such a substrate will generally be rendered liquid impervious by treating or coating one surface thereof or by laminating the flexible substrate with another liquid impervious substrate to render the total chassis liquid impervious. In this instance, the chassis itself serves as the "backsheet" for the training pants article.

A typical disposable training pants product is shown in FIG. 5 of the drawing. Such a product comprises an outer layer, 60, affixed to a lining layer, 61, by adhesion along the peripheral zones thereof. For example, the inner lining, 61, may be affixed to the outer layer, 60, along the periphery of leg band area, 62; along the periphery of leg band area, 63; and along the periphery of waistband area, 64. Affixed to the crotch area of the article is a generally rectangular absorbent core, 65, comprising an absorbent composite structure of the present invention. Typical training pants products of this kind are described in Roberts; U.S. Pat. No. 4,619,649; Issued Oct. 28, 1986, incorporated herein by reference.

TEST METHODS

In describing the present invention, characteristics of the staple fiber component such as water retention value and characteristics of the polymeric gelling agent such as gel volume are set forth. Where reported, these characteristics can be determined using the following test methods:

WATER RETENTION VALUE (WRV)

A sample of about 0.3 g to about 0.4 g of fibers is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover, and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value is calculated as follows:

$$WRV = \frac{(W - D)}{D} \times 100$$

where,
W = wet weight of the centrifuged fibers;
D = dry weight of the fibers; and
W − D = weight of absorbed water.

GEL VOLUME IN ARTIFICIAL MENSES

Gel volume in artificial menses is determined as the weight (grams) of artificial menses which will be absorbed per gram of polymeric gelling agent. Such a determination is first made after two minutes of contact between gelling agent and artificial menses to give an indication of the speed with which the gelling agent takes up fluid. A determination is then made after an extended period (60 minutes) of contact between gelling agent and artificial menses in order to determine an equilibrium gel volume value.

Artificial menses employed in the gel volume comprises a mixture of sheep's blood and a synthetic mucous component. Each of these components and their preparation is described as follows:

I. Artificial Menses Components

A. Mucous
   31.0 g gastric mucin (ICN Biomedicals, Inc.)
   2.0 ml prepared lactic acid solution
   7.5 ml prepared potassium hydroxide solution
   450 ml prepared phosphate buffered saline solution
B. Blood 500 ml sterile defibrinated sheep blood (Cleveland Scientific)

II. Preparation

A. Lactic Acid Solution
   1:10 dilution of 85-95% lactic acid:distilled water
B. Potassium Hydroxide Solution
   10% (by weight) potassium hydroxide in distilled water
C. Phosphate Buffered Saline Solution
   1. Solution A:
      1.42 g anhydrous dibasic sodium phosphate
      8.50 g sodium chloride
      Add distilled water to a volume endpoint of 1 liter
   2. Solution B:
      1.38 g hydrous monobasic sodium phosphate
      8.50 g sodium chloride
      Add distilled water to a volume endpoint of 1 liter
   3. Start with 450 ml of Solution A and add Solution B to raise the pH to an endpoint of 7.2.
D. Mucous Component
   1. Combine ingredients outlined in IA.
   2. Stir (and gently heat, if necessary) to solublize.
   3. Autoclave @ 121° C. for 15 minutes.
   4. Let solution cool.
E. Artificial Menses Fluid
   1. Mix the mucous and blood components together.
   2. Solution must be refrigerated and brought to room temperature before using.
   3. Use within seven days due to blood aging.

Using artificial menses prepared as indicated, gel volume values are determined by a procedure wherein particles of polymeric gelling agent (PGA), held in a paper "teabag", are soaked in artificial menses fluid and are then centrifuged to remove the fluid which has not been imbibed by the PGA particles. The equipment, procedure and calculations employed in such a procedure are described as follows:

A. Equipment

Sample holders—glass cylinders (1.4 cm inside diameter, 3.4 height)
Centrifuge tubes—double chambered vessels wherein a first chamber is separated from the second chamber by a steel mesh seat for holding PGA-containing teabags
Teabag material—cut to 5.0 cm × 8.0 cm rectangles
Balance—0.0001 g sensitivity range
Fluid bath—200 ml of swelling fluid in a 90 × 50 Pyrex crystallizing dish
Centrifuge—Clinical model, with variable speed and a horizontal rotor with four 29.4 mm × 95 mm (I.D. × Depth) shields
Tachometer—with adapter for measuring centrifuge speed
Drying beakers—10 ml volume

B. Procedure

1. Teabags are inserted into sample holders and "Initial Teabag" weights are recorded.
2. Samples of PGA are weighed out to 0.0255 g ± 0.0005, and "Initial PGA" weights are recorded.
3. Samples are placed in an agitated fluid bath. Liquid is pipetted over the top of the PGA to insure fluid contact and to prevent gel blockage (teabag is also completely saturated with fluid).
4. Samples are equilibrated in the bath for one hour or two minutes, depending upon which type of gel volume measurement is being made.
5. Samples are then removed from the bath. Teabags containing PGA are carefully removed from the holders and placed in the centrifuge tubes.
6. Samples are centrifuged at 125 gravities (g's) force for 10 minutes. The 10 minute time does not include the time needed for the centrifuge to reach 125 g's (1 minute, depending on the centrifuged used).
7. Samples are removed from the centrifuge tubes and weighed. The "(Wet PGA + Wet Teabag)" weights are recorded.

C. Calculations

Gel Volume can be expressed as the weight fraction of the amount of swelling fluid absorbed to the initial weight of PGA. Gel volume is defined as follows relative to experimentally measured and calculated parameters.

Gel Volume—Centrifugation

The Gel Volume—Centrifugation (GVC) is calculated with the following equation $$GVC = \frac{Wet\ PGA - Initial\ PGA}{Initial\ PGA}$$

where the Initial PGA is the PGA sample weighed in Procedure Step #2, and the Wet PGA is the swelled PGA sample after centrifugation. The Wet PGA (WPGA) is calculated using:

$$WPGA = [(WPGA + WTB) - WTB]$$

where (WPGA+WTB) is the quantity weighed in Procedure Step #7, and WTB is the Wet Teabag. Since the wet teabag also includes some solids from the fluid, WTB is calculated using:

$$WTB = (ITB)(WTB\ factor)$$

where ITB is the Initial Teabag weight in Procedure Step #1, and the WTB factor is obtained from a calibration curve. The WTB curve for artificial menses is generated by the following equation for centrifugal force values within the ranges of 120 to 301 g's.

$$WTB\ Factor = [-0.00109 \times Centrifugal\ Force\ (g's)] + 1.85127$$

GEL VOLUME IN SYNTHETIC URINE

Gel volume in terms of grams of synthetic urine absorbed per gram of polymeric gelling agent is determined by swelling the polymer samples in several aliquots of synthetic urine. The amount of such synthetic urine actually absorbed by the polymeric gelling agent is determined by a procedure which involves use of a synthetic urine solution containing Blue Dextrin so that optical absorbence measurements can be used to calculate the amount of synthetic urine that is not taken up by the hydrogel which forms.

(a) Blue Dextrin Solution Preparation

A 0.03% Blue Dextrin (BD) solution is prepared by dissolving 0.3 parts of Blue Dextrin (Sigma D-5751) in 1000 parts of Synthetic Urine (SU) solution. Synthetic Urine is 15.0 parts of 1% TRITON X-100, 60.0 parts of NaCl, 1.8 parts of $CaCl_2.2H_2O$, and 3.6 parts of $MgCl_2.6H_2O$, diluted to 6000 parts with distilled $H_2O$. The resulting solution has an absorbence of about 0.25 at its absorbence maximum of 617 nm.

(b) Hydrogel Equilibration

Aliquots of the hydrogel-forming polymeric gelling agent to be tested are swelled in (i) 20 parts of Synthetic Urine (SU) solution and (ii) 20 parts of Blue Dextrin (BD) solution. The suspension in the Blue Dextrin (BD) solution is prepared in duplicate. For most hydrogels, 0.1–0.25 parts of hydrogel-forming dried powder is required to give a sufficiently high spectrophotometer reading relative to the Blue Dextrin reference solution. One hour of equilibration at ambient temperature under gentle stir-bar stirring is sufficient for swelling equilibrium to be attained. After equilibration, a 3 ml aliquot of supernatant is separated from each gel suspension by decantation followed by centrifugation. Two minute gel volume readings can be obtained by swelling the polymeric gelling agent for only two minutes.

(c) Gel Volume Determination

The optical absorbency (ABS) of each supernatant is determined spectrophotometrically with an accuracy of 0.001 absorbence units. The Synthetic Urine solution is used as an ABS=0.0 reference. The absorbency of the supernatant from the synthetic urine suspension without Blue Dextrin should not exceed 0.01 A; higher values indicate scattering from residual hydrogel gel particles or residual additives, and further centrifugation is necessary. The absorbency of the Blue Dextrin supernatants should exceed the absorbency of the Blue Dextrin reference solution by at least 0.1 absorbence units. Absorbency values below this range indicate the need to adjust the amount of polymeric gelling agent used to prepare the gel suspension.

(d) Gel Volume Calculation

The Gel Volume in synthetic urine of the polymeric gelling agent in gms/gm is calculated from (i) the weight fraction of the polymeric gelling agent in the gel suspension and (ii) the ratio of the excluded volume to the total volume of the suspension. Since Blue Dextrin is excluded from the hydrogel due to its high molecular weight, this ratio is related to the measured absorbencies. The following equation is used to calculate the gel volume:

$$Gel\ Volume = \left[ \frac{(gms\ BD\ Solution)}{(gms\ polymeric\ gelling\ agent^*)} \right] \times \left[ 1 - \frac{(ABS\ BD\ solution)}{(ABS\ BD\ supernatant - ABS\ SU\ supernatant)} \right]$$

*Corrected to a dry weight basis

The absorbent web structures herein, as well as disposable absorbent articles containing them, are illustrated by the following examples. In these examples, reported density measurements are all made under a confining pressure of 0.0007 psi (0.005 kPa). Furthermore ±values where reported indicate deviation at the 95% confidence level.

EXAMPLES I-IX

A number of composite absorbent web structures are prepared from polypropylene microfibers, crimped polyethylene terephthalate (PET) staple fibers, fluid control system particles, and nonionic surfactant as a hydrophilizing agent. A more complete description of each of these components is given as follows:

Polypropylene Blown Microfibers (BMF)

Size = 5 microns in diameter (average)
Fiber Material Modulus = At least $0.9 \times 10^{10}$ dynes/cm$^2$

Staple Fibers

Type = KODEL PET marketed by Eastman
Size = 15 denier
Water Retention Value = 5%
Percent Crimp = 40%
Fiber Material Modulus = $3.0 \times 10^{10}$ dynes/cm$^2$
Average Fiber Length = 1.5 inch (3.8 cm)

Powdered Cellulose

Type = SOLKA-FLOC KS-1016 marketed by the James River Corporation
Particle Size = 0.1 mm mean length; 0.022 mm mean diameter
Aspect Ratio = 5:1

Polymeric Gelling Agent (PGA)

Type = Polyacrylate—WATERLOK J-550 marketed by Grain Processing Corp.
Size = less than 300 microns (avg.)
Equilibrium Gel Volume (Artificial Menses) = 35.8 g/g.
Two Minute Gel Volume (Artificial Menses) = 30.7 g/g.

Hydrophilizing Agent

Type = TRITON X-100 nonionic surfactant marketed by Rohm & Haas

To prepare these structures, PET staple fiber and fluid control system particles are admixed together and introduced into a stream of microfibers using an apparatus similar to that shown in the drawing hereinbefore described. The composite web structures which are prepared have the characteristics shown in Table I.

TABLE I

Absorbent Web Structures: Variation in Fluid Control System
Surfactant treatment: TRITON X-100 @ 1.0% by weight (target) of polypropylene fibers.

| Example No. | Powdered Cellulose Level (% by wt) | Web Basis Weight (g/m$^2$) | Component Basis Weight (g/m$^2$) | | | | Web Density (g/cm$^3$) |
|---|---|---|---|---|---|---|---|
| | | | Powdered Cellulose | PGA | BMF | PET Staple | |
| I | 10 | 211.1 | 21.1 | 0 | 57 | 133 | ~0.010 |
| II | 20 | 237.5 | 47.5 | 0 | 57 | 133 | ~0.013 |
| III | 30 | 271.4 | 81.4 | 0 | 57 | 133 | ~0.016 |
| IV | 40 | 316.7 | 126.7 | 0 | 57 | 133 | ~0.019 |
| V | 50 | 380.0 | 190.0 | 0 | 57 | 133 | ~0.024 |
| VI | 5 | 250.0 | 12.5 | 47.5 | 57 | 133 | ~0.015 |
| VII | 10 | 263.9 | 26.4 | 47.5 | 57 | 133 | ~0.016 |
| VIII | 20 | 296.9 | 59.4 | 47.5 | 77 | 133 | ~0.018 |
| IX | 30 | 339.3 | 101.8 | 47.5 | 57 | 133 | ~0.021 |

The web structures described in Table I are all useful as absorbent cores in disposable absorbent articles of especially desirable comfort properties. Furthermore, such structures have excellent fluid acquisition and distribution characteristics. Those structures containing polymeric gelling agents (Examples VI-IX) hold acquired body fluids in an especially tenacious manner by virtue of the fluid gelling properties of the gelling agents therein.

of fluid uptake in grams/m$^2$/minute. This initial rate is defined as the initial slope of the fluid uptake versus time plot, normalized over the area of contact between the sample and frit (g/m$^2$/min) The initial slope is determined by linear regression of data points collected during the first 1.5 minutes of the capillary sorption test. If the correlation coefficient is greater than or equal to 0.98 the slope is used to calculate the initial rate. If it is not, data points are discarded until regression analysis yields a correlation coefficient that satisfies the 0.98 criterion.

Capillary sorption initial rate data for several types of absorbent web structures are set forth in Table II. Each data point for initial rate represents an average taken from the testing of five webs.

TABLE II

Capillary Sorption Initial Rate Determinations
Surfactant treatment: TRITON X-100 at 1.0% by weight (target) of polypropylene fibers

| Web Sample No. | Component Basis Weight (g/m$^2$) | | | | Total Particulate Load (% by wt Powdered Cellulose + PGA) | Web Density 0.5 psi (g/cm$^3$) | Initial Rate @ (g/m$^2$/min) |
|---|---|---|---|---|---|---|---|
| | Powdered* Cellulose | 15-den PET Staple | PGA** | BMF*** | | | |
| 1 | — | 95 | — | 95 | 0 | 0.011 | 567 (±46) |
| 2 | — | 95 | 35 | 95 | 16 | 0.011 | 631 (±54) |
| 3 | 25 | 95 | — | 95 | 12 | ~0.011 | 714 (±19) |
| 4 | 50 | 95 | — | 95 | 21 | ~0.012 | 858 (±49) |
| 5 | 120 | 95 | — | 95 | 39 | 0.021 | 1110 (±82) |
| 6 | 25 | 95 | 35 | 95 | 24 | ~0.013 | 779 (±38 |
| 7 | 50 | 95 | 35 | 95 | 31 | ~0.015 | 930 (±20) |
| 8 | 120 | 95 | 35 | 95 | 45 | 0.022 | 1152 (±23) |

*SOLKA-FLOC KS-1016 marketed by the James River Corporation
**AQUALIC polyacrylate marketed by Nippon Shokubai KK Equilibrium Gel Volume (artificial menses) = 28.9 g/g
***Polypropylene microfibers as used in Examples I-IX

EXAMPLE X

Absorbent properties of the microfiber-based absorbent web structures of the present invention can be demonstrated by a zero head capillary sorption test. In such testing, samples of absorbent webs (28.27 cm$^2$) are placed on a 6 cm diameter glass frit [Por E (ASTM 4-8 micron) from Ace Glass] and are maintained in contact with a reservoir containing synthetic urine. The height of the frit and height of the reservoir are adjusted to the same level. A confining weight of 0.5 psi is placed on top of each structure sample.

Using this setup, the number of grams of fluid taken up by the web structure as a function of time can be determined. It is also possible to calculate an initial rate The Table II data indicate that the addition of powdered cellulose hydrophilic entities to microfiber webs containing crimped PET staple fibers, whether or not such webs also contain polymeric gelling agent, provides a significant increase in initial rate of acquisition of aqueous body fluid.

EXAMPLE XI

The ability of the absorbent web structures of this invention to accept, distribute and contain fluid can be demonstrated by means of a drip test. In such a test, a circular cross section of web structure (7.62 cm in diameter) is placed on a large mesh wire screen. Fluid, e.g., synthetic urine, is introduced at the rate of 0.10 ml/sec. into the center of the structure from a point source beginning at a time t=0. The time to failure is then measured as the time at which fluid is first observed to leak out the bottom of the structure. Results are presented as "Time to Failure" and are reported in seconds. Web structures which tested are those from Example X, Table II. Drip test results are set forth in Table III.

TABLE III
EFFECT OF POWDERED CELLULOSE LOADING ON FLUID DISTRIBUTION DRIP TEST ANALYSIS AT ZERO CONFINING WEIGHT

| | |
|---|---|
| Fluid: | Synthetic Urine |
| Confining Weight: | 0, "no load" |
| BMF: | Polypropylene at 5 micron average diameter |
| Surfactant Treatment: | TRITON X-100 at 1% (target) by weight of BMF |
| Powdered Cellulose: | SOLKA-FLOC KS-1016 |
| Time to Failure: | time before fluid leaks out bottom of sample |

| Sample No. | % by wt. Powdered Cellulose | Powdered Cellulose | 15-den PET Staple | BMF | Time to Failure (seconds) |
|---|---|---|---|---|---|
| | | Component Basis Weight (g/m²) | | | |
| X(1) | 0 | — | 95 | 95 | 28 (±21) |
| X(5) | 39 | 120 | 95 | 95 | 338 (±10) |

The time to failure data in Table III represents the average of five web structures. The data indicate that the addition of powdered cellulose to a microfiber/staple fiber web can significantly enhance the propensity of the web to distribute and store acquired fluid throughout the web structure.

EXAMPLE XII

The ability of the composite structures of this invention to contain a fluid load against gravitational pressure is determined by means of a containment efficiency test. In such a test, a web structure sample is prepared for testing by first cutting it into a 3.75 inch (9.53 cm) square. A fluid impervious polyethylene backsheet (3.9"×3.75", i.e., 9.9 cm×9.53 cm) is then attached to the bottom of the web sample by sealing along two sides of the web sample with double sided tape. A 20 ml load of fluid is then introduced by pouring the fluid directly into the center of the sample. The web is then held in the air on its side for 30 seconds such that fluid can drain out along one of its unsealed edges. After 30 seconds of drain time, the web is weighed to determine the amount of fluid left in the sample. Containment Efficiency is reported as the percent of initial fluid load held in the sample against gravity. No external confining pressure is applied to the sample during the test. Artificial menses is used as the test fluid.

A description of the web samples (from Example X, Table II) which are tested and Containment Efficiency results are set forth in Table IV.

TABLE IV
EFFECT OF POWDERED CELLULOSE LOADING ON FLUID CONTAINMENT CONTAINMENT EFFICIENCY TEST ANALYSIS

| | |
|---|---|
| Test Fluid: | Artificial Menses |
| Confining Weight: | 0 psi, "no load" |
| Fluid loading: | 20 ml |
| Sample Size: | 3.75" × 3.75" |
| Containment Efficiency: | % of loaded fluid held in pad against gravity after 30 sec |
| BMF: | Polypropylene at 5 micron average diameter |
| Surfactant Treatment: | TRITON X-100 at 1% (target) by weight of BMF |
| PGA: | AQUALIC Polyacrylate, Equilibrium Gel Volume = 26.9 g/g |
| Powdered Cellulose: | SOLKA-FLOC KS-1016 |

| Sample No. | Component Basis Weight (g/m²) | | | | % by wt. Powdered Cellulose + PGA | Containment Efficiency (% of initial loading) |
|---|---|---|---|---|---|---|
| | Powdered Cellulose | 15-den PET Staple | PGA | BMF | | |
| X(1) | — | 95 | — | 95 | 0 | 60 (±7) |
| X(2) | — | 95 | 35 | 95 | 16 | 63 (±9) |
| X(3) | 25 | 95 | — | 95 | 12 | 66 (±5) |
| X(4) | 50 | 95 | — | 95 | 21 | 76 (±5) |
| X(5) | 120 | 95 | — | 95 | 39 | 100 (±0) |
| X(6) | 25 | 95 | 35 | 95 | 24 | 71 (±4) |
| X(7) | 50 | 95 | 35 | 95 | 31 | 94 (±5) |
| X(8) | 120 | 95 | 35 | 95 | 45 | 100 (±0) |

Each data point in Table IV represents the average of four web structure measurements. The Table IV data illustrate that addition of increasing amounts of hydrophilic particulate entities to microfiber/staple fiber composite webs can significantly enhance the fluid containment efficiency of such structures. Containment efficiency is especially enhanced when the web structures also contain particles of polymeric gelling agents.

EXAMPLE XIII

A sanitary napkin employing an absorbent structure of this invention is prepared as follows:

A composite absorbent structure is prepared in the general manner described in Example VIII, having a caliper of about 1.7 cm and a density of about 0.018 g/cm³ as measured under a confining pressure of 0.0007 psi (about 4.9 N/m²). This structure is cut into a rectangular web of 7 in.×2.5 in. (about 18 cm×6.4 cm). This web is placed against a waterproof backing sheet (9 in.×3 in.) of embossed polyethylene having an embossed caliper of about 2.4 mils. The web and backsheet are wrapped in a formed film polyethylene (DRI-WEAVE) having a caliper of about 17.2 mils. The web is bonded to the topsheet with a 0.001 in. film of water soluble adhesive. The ends of the resulting sanitary napkin are heat sealed and tapered. A 7 in. × 1.5 in. strip of adhesive is placed on the underside of the sanitary nature of the fluid control system on sanitary pad resilience is shown.

TABLE V

EFFECT OF POWDERED CELLULOSE AND POWDERED CELLULOSE + PGA LOADING ON RESILIENCE
EDGEWIDE RESILIENCE ANALYSIS OF SANITARY PADS

| Type of Pad Core | Component Basis Weight (g/m²) | | | | Dry Resilience (% strain recovered) | Wet Resilience (% strain recovered) |
|---|---|---|---|---|---|---|
| | Powdered Cellulose | 15-den PET Staple | PGA | BMF | | |
| Control* 100% Fluff | | | | | 66 (±7) | 27.5 (±4.5) |
| Table II No. 1 | — | 95 | — | 95 | 92 (±2) | 84 (±4) |
| Table II No. 2 | — | 95 | 35 | 95 | 92 (±3) | 82 (±5) |
| Table II No. 3 | 25 | 95 | — | 95 | 92 (±8) | 80 (±2) |
| Table II No. 6 | 25 | 95 | 35 | 95 | 89 (±5) | 79 (±4) |
| Table II No. 5 | 120 | 95 | — | 95 | 91 (±7) | 70 (±6) |
| Table II No. 8 | 120 | 95 | 35 | 95 | 90 (±7) | 71 (±7) |

*Core from ALWAYS Maxi, a commercially marketed sanitary pad having a tubular chassis.

napkin and covered with a 8 in. × 2 in. piece of release paper. The top side of the sanitary napkin is sprayed with 0.01 g of a nonionic surfactant. The resultant absorbent article is useful as a sanitary napkin having especially desirable comfort and absorbent properties.

EXAMPLE XIV

Examples X–XII illustrate that microfiber-based, PET staple fiber-containing sorbent web structures of improved fluid handling properties can be prepared by adding powdered cellulose hydrophilic entities to such structures. In this example, the effect of such powdered cellulose hydrophilic entities on web resilience properties is demonstrated.

The resilience characteristics of sanitary napkins prepared as generally described in Example XIII (without the underside adhesive/release paper combination) can be demonstrated by the testing procedures hereinbefore described which involve edgewise compression of such products followed by removal of the compressive force to allow the sanitary pad to relax. Thus sanitary pads of a given standard initial width (i.e., 2.5 inches) are compressed in the cross direction to the 60% strain level (i.e., a width of 1.0 inch or 40% of the initial width) for a period of three hours. The compressive force is then removed, and after a relaxation period of five minutes, the final width of the pad is measured. A percent resilience is then calculated using the equation hereinbefore set forth. For Example XIII pads having an initial width of 2.5 inches and a 1.5 inch strain level, percent resilience is calculated as follows:

$$\% \text{ Resilience} = \left[1 - \frac{(2.5 - \text{Final Width})}{1.5}\right] \times 100$$

wherein Final Width is measured in inches. The % Resilience values can be measured for sanitary napkins in both the wet (e.g., containing 5 ml of artificial menses) and dry states.

Using the foregoing procedures, % resilience values are calculated for sanitary napkins of the general Example XIII type having different kinds of absorbent cores. Results are shown in Table V wherein the effect of the The Table V data show that sanitary pads prepared from microfiber-based absorbent web structures have a 15-denier PET staple fiber component possess desirable antibunching or resilience properties relative to pads prepared with absorbent structures containing cellulose fluff fibers. While the fluff core displays poor dry resilience, it is especially deficient when tested in a wet state. On the other hand, the microfiber composite cores show minimal difference between dry and wet resilience. This is hypothesized to be due primarily to the function of the relatively stiff PET staple fibers, which are essentially nonabsorbent and do not undergo a significant dry to wet modulus change. The Table V data further show that addition to such microfiber cores of even relatively large amounts of the particulate fluid control system has minimal adverse effect on the desirable resilience properties of such structures vis-a-vis 100% fluff.

EXAMPLE XV

Another form of sanitary napkin employing an absorbent structure of this invention is prepared in an hourglass-shaped configuration with "wings" and a tissue layer. To prepare such a structure, a tissue layer having an overall basis weight of 24.4 g/m² is cut in an hourglass shape such that its overall length is 8.5 inches, the center width is 3 and ⅜ inches, and the end widths are 3 and ⅞ inches. This tissue layer is bonded against a waterproof backing sheet of embossed polyethylene (having an embossed caliper of about 2.4 mils) using a ¼ inch wide strip of double-sided adhesive tap.

A composite web structure as described in Table II, Sample 8 is used as an absorbent core. Such a structure has a caliper of 1.68 cm and a density of 0.022 g/cm³ as measured under a confining pressure of 0.0007 psi. This core is cut in an hourglass shape such that its overall length is 8.25 inches, its center width is 2.2 inches, and its overall area is 20.6 square inches. This core layer is then bonded to the tissue layer using a ¼ inch wide strip of double-sided adhesive tape.

The top side of the core is then bonded to a formed film polyethylene DRI-WEAVE topsheet with a 0.001 inch film of water soluble adhesive. This layered structure is then heat sealed (seal forms between topsheet and backsheet) with the core centered. A cut is then made along the heat seal such that final product dimensions are 9.5 inches in length, 4.5 inches in width at the ends, and 7 inches in width at the center where the product wings are located. A 8.25 inch by 2 inch strip of adhesive is placed on the underside of the sanitary napkin and covered with a 9 inch by 2.25 inch piece of release paper. Adhesive pieces 1 inch by 1 inch are placed on the underside of each wing and covered with 1.25 inch by 1.25 inch pieces of release paper. The top side of the sanitary napkin is sprayed with 0.01 grams of nonionic surfactant. The resulting absorbent article is useful as a sanitary napkin having especially desirable comfort and fluid handling properties.

EXAMPLE XVI

Both the absorbent performance and resilience properties of sanitary pads prepared with the absorbent structures of the present invention are demonstrated by consumer panel testing wherein panelists actually wear the products being evaluated. Such panel testing is conducted as a comparison of three products of the general Example XV configuration worn in rotation during menstrual use (panelists wear pads according to their own habits during menstruation). Soiling and bunching data are tabulated from technical grading of returned pads and panties.

Criteria for soil and bunch grades are set forth as follows:

Soil Grading a. Overall Soiling Incidence (% of worn pads): This refers to the percentage of any worn pads that result in any type of panty soil and is reported on a per product basis.
b. Heavy Load—Soil Incidence (% of pads w/9+gram load): This refers to the percentage of worn pads that have been loaded with 9 grams or more of menses, that result in any type of panty soil and is reported on a per product basis.
c. Heavy Load—% Moderate+% Severe Soil Incidence: This refers to the percentage of worn pads that have been loaded with 9 grams or more of menses, that resulted in only moderate and severe soils and is reported on a per product basis.

Bunch Grading

The incidence and severity of pad bunching are graded according to the "returned pad analysis" guidelines for none, slight, moderate, and severe bunching as listed below. In order to collect pad bunching data, panelists return used pads (still attached to the panty). The core width is then measured in the center of the pad, and the percent bunching is calculated as the percentage of the initial core width (2.2 inches) that has been bunched. The Bunch Grade is presented as the percent of all used pads yielding a measured bunch value of less than 10% (reported on a per product basis).

Bunch Grades

None: less than 10% of pad is bunched
Slight: 10%–30% of pad is bunched
Moderate: 30%–50% of pad is bunched
Severe: $\geq$50% of pad is bunched Sanitary pads of the general Example XV type but with different types of absorbent cores are tested in menstrual-use panel testing for soiling and bunching.

A description of the products employed, as well as test results, are set forth in Table VI:

TABLE VI

| Example No. | Product Core Type | Overall Soiling Incidence (% of worn pads) | Heavy Load Soiling Incidence (% of pads w/9 + g load) | Heavy Load % Moderate +% Severe Soil Incidence | Bunch Grade (% with none) |
| --- | --- | --- | --- | --- | --- |
| — | Fluff | 29 | 74 | 37 | 19 |
| Table II No. 5 | BMF/Staple/PC | 30 | 60 | 60 | 31 |
| Table II No. 8 | BMF/Staple/PGA/PC | 26 | 52 | 16 | 39 |

The Table IV data indicate that sanitary pads using absorbent web structures of the present invention compare very favorably in soiling protection to conventional sanitary pads employing a 100% air felt absorbent core. Such pads furthermore show a reduced tendency to bunch in comparison with the conventional pad.

EXAMPLE XVII

A diaper is prepared as described in U.S. Pat. No. 3,860,003, Buell, Issued Jan. 14, 1975, incorporated herein by reference, except that, in place of the absorbent diaper core disclosed therein (e.g., made from air-laid wood pulp) there is utilized as a core inserted between the top sheet and the backsheet an hourglass-shaped composite web structure of the present invention. The absorbent structure is made as described in Table I, Example IX. The gel volume of the J-550 PGA is approximately 60 grams of synthetic urine per gram of gelling agent. The basis weight of the structure is 339.3 gm/m$^2$; the density is 0.02 gm/cm$^3$, resulting in a core thickness of 1.6 cm, measured at a confining pressure of 0.0007 psi.

EXAMPLE XVIII

Absorbent web structures of the present invention are made with polypropylene microfibers, crimped PET staple fibers, acrylic acid grafted starch hydrogel having a weight average particle size of about 25 microns (SANWET IM-1000, from Sanyo Co., Japan) and particles of SOLKA-FLOC KS-1016 powdered cellulose using the process described in Example I. The SANWET IM-1000 has a gel volume of approximately 48 grams of synthetic urine per gram of gelling agent. The absorbent structures have a basis weight of 340 gm/m$^2$ and a caliper of ~1.6 cm which corresponds to a density of ~0.02 gm/cm$^3$. The structures are covered with a sheet of envelope tissue and cut to a size of 3.5 in.×15.5 in. (about 9×40 cm).

Absorbent structures of this type are then used as inserts in diaper products prepared as described in U.S. Pat. No. 3,860,003, Buell, Issued Jan. 14, 1975, incorporated herein by reference. The hourglass-shaped soft wood pulp cores of the diapers have the following dimensions: length: 15.5 in. (about 40 cm), width at the ears: 10.5 in. (about 27 cm), and width in the center: 3.75 in. (about 9.5 cm). The absorbent web structures of this invention are inserted lengthwise into the above-described diapers, in between the hourglass-shaped core and the polyethylene backing sheet, the envelope tissue against the hourglass-shaped core.

Such inserts improve the absorbent capacity of these diapers for urine.

What is claimed is:

1. An absorbent composite structure especially suitable for use in disposable absorbent articles of improved comfort, integrity and fluid handling characteristics, said composite structure comprising
   (A) from about 10% to 85% by weight of the composite of blown microfibers, substantially all of which are of a diameter less than about 50 microns, said microfibers being formed from synthetic polymeric material having a modulus value when dry of at least about $0.1 \times 10^{10}$ dynes/cm$^2$, said modulus value not diminishing significantly when said microfibers are wet;
   (B) from about 10% to 85% by weight of the composite of substantially nonabsorbent synthetic staple fibers, substantially all of which have a denier of from about 5 to 70 and a percent crimp of at least about 15%, said staple fibers being formed from a synthetic polymeric material having a modulus value when dry of at least about $0.1 \times 10^{10}$ dynes/cm$^2$, said modulus value not diminishing significantly when said staple fibers are wet;
   (C) from about 1% to 60% by weight of the composite of a fluid control system which comprises nongelling, hydrophilic particulate entities, substantially all of which have a greatest dimension ranging from about 0.01 mm to 10 mm and a ratio of greatest dimension to smallest dimension of 10:1 or less; and
   (D) from about 0.01% to 10% by weight of the composite of a hydrophilizing agent which serves to hydrophilize the microfibers, staple fibers and fluid control system components;
said hydrophilized microfibers, staple fibers and fluid control system components being combined in a manner which forms a composite web having a dry density of from about 0.006 to 0.10 g/cm$^3$.

2. An absorbent composite structure especially suitable for use in disposable absorbent articles of improved comfort, integrity and fluid handling characteristics, said composite structure comprising
   (A) from about 10% to 85% by weight of the composite of blown microfibers, substantially all of which are of a diameter less than about 50 microns, said microfibers being formed from synthetic polymeric material selected from polyolefins, polyesters, polyamides; polystyrenes and polyacrylics;
   (B) from about 10% to 85% by weight of the composite of substantially nonabsorbent synthetic staple fibers, substantially all of which have a denier of from about 5 to 70 and a percent crimp of at least about 15%, said staple fibers being formed from a synthetic polymeric material selected from polyolefins, polyesters, polyacrylics; polyamides and polystyrenes;
   (C) from about 1% to 60% by weight of the composite of a fluid control system which comprises
      (i) nongelling, hydrophilic particulate entities substantially all of which have a greatest dimension ranging from about 0.01 to 10 mm and a ratio of greatest dimension to smallest dimension of 10:1 or less; and
      (ii) nonfibrous particles of a hydrogel-forming polymeric gelling agent having an equilibrium gel volume of at least about 20 grams of artificial menses per gram of gelling agent and an extractable polymer content in synthetic urine of no more than about 17% by weight, substantially all of said polymeric gelling agent particles ranging in diameter from about 10 microns to 2 mm; said polymeric gelling agent particles being present in an amount such that the weight ratio of hydrophilic entities to polymeric gelling agent ranges from about 5:1 to 1:5; and
   (D) from about 0.01% to 10% by weight of the composite of a hydrophilizing agent which serves to hydrophilize the microfibers, staple fibers and fluid control system components; said hydrophilized microfibers, staple fibers and fluid control system components being combined in a manner which forms a composite web having longitudinal, transverse and thickness dimensions, said composite web having a dry density of from about 0.006 to 0.10 g/cm$^3$, with said composite web further exhibiting both wet and dry resilience properties which enable such a composite web to recover to at least 50% of its original transverse dimension after compression to a transverse dimension which is 40% of its original transverse dimension.

3. An absorbent composite structure according to claim 2 wherein
   (A) the nongelling, hydrophilic particulate entities comprise one or more materials selected from cellulose, cellulose derivatives, polyolefins, polyacrylics, polyesters, polyamides, polystyrenes, polyurethanes, clay, kaolin, talc, calcium carbonate, sodium sulfate, sodium carbonate and aluminum oxide;
   (B) the polymeric gelling agent is selected from hydrolyzed acrylonitrile grafted starch, acrylic acid grafted starch, polyacrylates, isobutylene-maleic anhydride copolymers and combinations thereof; and
   (C) the hydrophilizing agent is a nonionic surfactant.

4. An absorbent composite according to claim 3 which has a dry density of from about 0.006 to 0.04 g/cm$^3$.

5. An absorbent composite according to claim 4 wherein the weight ratio of microfiber component to staple fiber component ranges from about 1:3 to 3:1 and the weight ratio of nongelling hydrophilic particle entities to polymeric gelling agent particles ranges from about 4:1 to 1:1.

6. An absorbent composite according to claim 5 which comprises
   (A) from about 20% to 65% by weight of the composite of the blown microfiber component;
   (B) from about 10% to 60% by weight of the composite of the synthetic staple fiber component with substantially all of said staple fibers having a denier of from about 10 to 25; and
   (C) from about 15% to 55% by weight of the composite of a fluid control system which comprises hydrophilic particulate entities selected from powdered cellulose, microfiber microwebs, hydrophilic fibrids, particles of hydrophilic polyurethane foam and combinations of these hydrophilic particulate entities, substantially all of said hydrophilic particulate entities having a greatest dimension ranging from about 0.02 mm to 0.5 mm and having a ratio of greatest dimension to smallest dimension of about 5 or less.

7. An absorbent composite according to claim 6 wherein
(A) the microfibers utilized are polypropylene microfibers;
(B) the staple fibers utilized are polyethylene terephthalate staple fibers, substantially all of which have a fiber length between about 1.0 and 15 cm;
(C) the hydrophilic particulate entities utilized comprise powdered cellulose having an average greatest dimension ranging from about 0.05 mm to 0.3 mm and an average aspect ratio of 5 or less; and
(D) the polymeric gelling agent utilized is selected from slightly cross-linked, partially neutralized polyacrylates and acrylic acid grafted starch, has an equilibrium gel volume of at least about 25 grams of artificial menses per gram of polymeric gelling agent and has an extractable polymer content in synthetic urine of no more than about 10% by weight.

8. An absorbent article of improved comfort, integrity and fluid handling characteristics, said article comprising:
(A) a liquid impervious backing sheet;
(B) a liquid pervious hydrophobic topsheet; and
(C) an absorbent structure according to claim 1 positioned between said backing sheet and said topsheet.

9. An absorbent article of improved comfort, integrity and fluid handling characteristics, said article comprising:
(A) a liquid impervious backing sheet;
(B) a liquid pervious hydrophobic topsheet; and
(C) an absorbent core positioned between said backing sheet and said topsheet, said absorbent core comprising a composite web structure having longitudinal, transverse and thickness dimensions, said structure comprising
(i) from about 10% to 85% by weight of the structure of blown microfibers which have an average diameter of from about 1 to 10 microns, said microfibers being formed from synthetic polymeric material selected from polyolefins, polyesters, polyamides, polyacrylics and polystyrenes;
(ii) from about 10% to 85% by weight of the structure of substantially nonabsorbent synthetic staple fibers, substantially all of which have a denier of from about 10 to 25, and a percent crimp of at least about 15%, said staple fibers being formed from synthetic polymeric material selected from polyolefins, polyesters, polyacrylics, polyamides and polystyrenes;
(iii) from about 1% to 60% by weight of the composite of a fluid control system which comprises
(a) nongelling, hydrophilic particulate entities, substantially all of which have a greatest dimension ranging from about 0.01 mm to 10 mm and a ratio of greatest dimension to smallest dimension of 10:1 or less; and
(b) nonfibrous particles of a hydrogel-forming polymeric gelling agent having an equilibrium gel volume of at least about 20 grams of artificial menses per gram of gelling agent and an extractable polymer content in synthetic urine of no more than about 17% by weight, substantially all of said polymeric gelling agent particles ranging in diameter from about 30 microns to 2 mm; said polymeric gelling agent particles being present in an amount such that the weight ratio of hydrophilic entities to polymeric gelling agent ranges from about 5:1 to 1:5; and
(iv) from about 0.01% to 10% by weight of the structure of a hydrophilizing agent which serves to hydrophilize the microfibers, staple fibers, and fluid control system components;
said hydrophilized microfibers, staple fibers, and fluid control system components being combined in a manner which forms a composite structure having a dry density of from about 0.006 to 0.03 g/cm$^3$ with said composite web structure further exhibiting both wet and dry resilience properties which enable such a composite web structure to recover to at least 50% of its original transverse dimension after compression to a transverse dimension which is 40% of its original transverse dimension.

10. An absorbent article according to claim 9 wherein in the composite web structure component:
(A) the microfibers utilized are polypropylene microfibers;
(B) the staple fibers utilized are polyethylene terephthalate staple fibers, substantially all of which have a fiber length between about 1.0 and 15 cm;
(C) the hydrophilic particulate entities utilized comprise powdered cellulose having an average greatest dimension ranging from about 0.05 mm to 0.3 mm and an average aspect ratio of 5 or less; and
(D) the polymeric gelling agent utilized is selected from slightly cross-linked, partially neutralized polyacrylates and acrylic acid grafted starch, has an equilibrium gel volume of at least about 25 grams of artificial menses per gram of polymeric gelling agent and has an extractable polymer content in synthetic urine of no more than about 10% by weight.

11. An absorbent article according to claim 9 wherein within said absorbent core there is a concentration gradient of polymeric gelling agent particles with the zone of said core nearest the backing sheet having a relatively higher concentration of polymeric gelling agent than the zone of said core nearest the top sheet.

12. An absorbent article according to claim 9 wherein the absorbent core is of multi-layered configuration having an upper layer comprising air-laid cellulosic fibers containing from 0% to 10% by weight of said upper layer of polymeric gelling agent particles or fibers and further having a lower layer comprising said microfiber-containing composite web structure.

13. An absorbent article according to claim 9 wherein the absorbent core is of multi-layered configuration having a lower layer comprising air-laid cellulosic fibers containing from 0% to 10% by weight of said lower layer of polymeric gelling agent particles or fibers and further having an upper layer comprising said microfiber-containing composite web structure.

14. An absorbent article according to claim 9 wherein said composite absorbent structure is positioned underneath the topsheet as an upper layer and a laminate structure is positioned on top of the backing sheet as a lower layer, said laminate structure itself consisting essentially of at least one layer of dispersed particles of polymeric gelling agent material overwrapped with sheets of tissue.

15. An absorbent article according to claim 9 in the form of a sanitary napkin wherein, in the composite web structure component,
(A) the blown microfibers comprise from about 25% to 50% by weight of the web structure;
(B) the synthetic staple fibers comprise from about 20% to 50% by weight of the web structure; and
(C) the fluid control system comprises from about 20% to 50% by weight of the web structure.

16. An absorbent article according to claim 12 in the form of a sanitary napkin wherein one or more of the layers of the absorbent core are overwrapped in envelope tissue.

17. An absorbent article according to claim 9 in the form of a disposable diaper wherein in the composite web structure component
(A) the blown microfibers comprise from about 25% to 65% by weight of the web structure;
(B) the synthetic staple fibers comprise from about 10% to 50% by weight of the web structure;
(C) the fluid control system comprises from about 20% to 55% by weight of the web structure; and
(D) the polymeric gelling agent component of the fluid control system has a gel volume of from about 20 to 70 grams of synthetic urine per gram of gelling agent.

18. A disposable diaper according to claim 17 wherein
(A) said topsheet is coextensive with one face of said core;
(B) said backing sheet is coextensive with the face of the core opposite the face covered by said topsheet and has a width greater than that of the core, to thereby provide side marginal portions of the backing sheet which extend beyond the core; and
(C) said absorbent core is hourglass-shaped.

19. An absorbent article according to claim 12 in the form of a disposable diaper wherein
(A) said topsheet is coextensive with one face of said absorbent core;
(B) said backing sheet is coextensive with the face of the absorbent core opposite the face covered by said topsheet and has a width greater than that of the absorbent core, to thereby provide side marginal portions of the backing sheet which extend beyond the absorbent core;
(C) the upper layer of the absorbent core is hourglass-shaped; and
(D) the polymeric gelling agent component of the fluid control system has a gel volume of from about 20 to 70 grams of synthetic urine per gram of gelling agent.

20. Disposable training pants of improved comfort, integrity and fluid handling characteristics, said training pants comprising
(A) a nonwoven, flexible substrate fashioned into a chassis in the form of briefs or shorts; and
(B) an absorbent core affixed in the crotch area of said chassis, said absorbent core comprising a composite web structure according to claim 2 with the polymeric gelling agent material utilized in said absorbent core having a gel volume of from about 20 to 70 grams of synthetic urine per gram of gelling agent.

* * * * *

UNITED STATES PATENT AND TRADEMARK OFFICE
CERTIFICATE OF CORRECTION

PATENT NO. : 4,865,596
DATED : September 12, 1989
INVENTOR(S) : Paul T. Weisman, Thomas H. Daugherty It is certified that error appears in the above-identified patent and that said Letters Patent is hereby corrected as shown below:

On the cover sheet, the Assistant Examiner's name should be --Mark O. Polutta--.

Column 17, line 40, "rebellions" should be --regions--.

Column 25, Table I, for the Basis Weight in the BMF column for Example VIII, "77" should be --57--.

Column 26, in Table II, the headings for the columns should be as follows:

| Web Sample No. | Component Basis Weight (g/m$^2$) | | | | Total Particulate Load (% by wt Powdered Cellulose + PGA) | Web Density (g/cm$^3$) | Initial Rate @ 0.5 psi (g/m$^2$/min) |
|---|---|---|---|---|---|---|---|
| | Powdered* Cellulose | 15-den PET Staple | PGA** | BMF*** | | | |

Column 35, line 52, "10to" should be --10 to--.

Signed and Sealed this

Twentieth Day of November, 1990

Attest:

HARRY F. MANBECK, JR.

Attesting Officer

Commissioner of Patents and Trademarks